United States Patent
Hirose et al.

(10) Patent No.: US 12,266,099 B2
(45) Date of Patent: Apr. 1, 2025

(54) OPHTHALMOLOGICAL INFORMATION PROCESSING APPARATUS, OPHTHALMOLOGICAL APPARATUS, OPHTHALMOLOGICAL INFORMATION PROCESSING METHOD, AND RECORDING MEDIUM

(71) Applicant: Topcon Corporation, Tokyo (JP)

(72) Inventors: Ryoichi Hirose, Tokyo (JP); Tatsuo Yamaguchi, Warabi (JP)

(73) Assignee: TOPCON CORPORATION, Tokyo (JP)

( * ) Notice: Subject to any disclaimer, the term of this patent is extended or adjusted under 35 U.S.C. 154(b) by 582 days.

(21) Appl. No.: 17/580,643

(22) Filed: Jan. 21, 2022

(65) Prior Publication Data
US 2022/0142468 A1    May 12, 2022

Related U.S. Application Data

(63) Continuation of application No. PCT/JP2020/020478, filed on May 25, 2020.

(30) Foreign Application Priority Data

Jul. 23, 2019  (JP) .................................. 2019-135240

(51) Int. Cl.
G06T 7/00    (2017.01)
G06T 5/00    (2024.01)

(52) U.S. Cl.
CPC .............. *G06T 7/0012* (2013.01); *G06T 5/00* (2013.01); *G06T 2207/10024* (2013.01);
(Continued)

(58) Field of Classification Search
CPC ................................ G06T 7/0012; G06T 5/00
See application file for complete search history.

(56) References Cited

U.S. PATENT DOCUMENTS

| 5,971,767 A | 10/1999 | Kaufman et al. |
| 6,331,116 B1 | 12/2001 | Kaufman et al. |
| (Continued) | | |

FOREIGN PATENT DOCUMENTS

| JP | 2004-510515 A | 4/2004 |
| JP | 2011-025046 A | 2/2011 |
| (Continued) | | |

OTHER PUBLICATIONS

International Search Report and Written Opinion mailed on Jul. 14, 2020, received for PCT Application PCT/JP2020/020478, Filed on May 25, 2020, 9 pages including English Translation.
(Continued)

*Primary Examiner* — Kevin Ky
(74) *Attorney, Agent, or Firm* — XSENSUS LLP

(57) ABSTRACT

An ophthalmological information processing apparatus includes an acquisition unit and an image correcting unit. The acquisition unit is configured to acquire a front image depicting a predetermined site of a subject's eye in multiple gradations and an OCT image of the subject's eye. The image correcting unit is configured to correct a pixel value in a region including a first position of the predetermined site in the OCT image based on a pixel value at a second position corresponding to the first position in the front image.

21 Claims, 17 Drawing Sheets

(52) U.S. Cl.
CPC .............. *G06T 2207/10101* (2013.01); *G06T 2207/30004* (2013.01); *G06T 2207/30041* (2013.01)

(56) References Cited

U.S. PATENT DOCUMENTS

| | | |
|---|---|---|
| 6,343,936 B1 | 2/2002 | Kaufman et al. |
| 2001/0031920 A1 | 10/2001 | Kaufman et al. |
| 2002/0039400 A1 | 4/2002 | Kaufman et al. |
| 2002/0045153 A1 | 4/2002 | Kaufman et al. |
| 2007/0103464 A1 | 5/2007 | Kaufman et al. |
| 2007/0167718 A1 | 7/2007 | Kaufman et al. |
| 2007/0276225 A1 | 11/2007 | Kaufman et al. |
| 2007/0291277 A1* | 12/2007 | Everett .............. G01B 9/02077 356/497 |
| 2011/0181702 A1 | 7/2011 | Hauger et al. |
| 2011/0199579 A1 | 8/2011 | Muto |
| 2012/0188510 A1 | 7/2012 | Suehira et al. |
| 2012/0320339 A1 | 12/2012 | Yonezawa |
| 2013/0003016 A1* | 1/2013 | Feldon .................... A61B 3/14 351/246 |
| 2014/0303499 A1 | 10/2014 | Toma et al. |
| 2015/0010226 A1* | 1/2015 | Kubota ................ A61B 3/1233 382/131 |
| 2015/0216408 A1 | 8/2015 | Brown et al. |
| 2015/0272432 A1* | 10/2015 | Satake ................ A61B 3/0025 351/246 |
| 2016/0284103 A1* | 9/2016 | Huang ................ A61B 5/0066 |
| 2016/0302664 A1* | 10/2016 | Yamakawa ............ A61B 3/102 |
| 2016/0331224 A1* | 11/2016 | Uji ........................ A61B 3/0025 |
| 2018/0028056 A1* | 2/2018 | Kubota .................... G06T 7/12 |
| 2018/0092528 A1* | 4/2018 | Takeno .................. A61B 3/102 |
| 2018/0122077 A1* | 5/2018 | Wada ........................ G06T 5/70 |
| 2018/0153401 A1* | 6/2018 | Strózyk .................. A61B 3/117 |
| 2018/0242839 A1* | 8/2018 | Fukuhara .............. A61B 3/102 |
| 2018/0289257 A1* | 10/2018 | Ikegami ................ A61B 3/1225 |
| 2019/0059720 A1* | 2/2019 | Kubota ................ A61B 3/0025 |
| 2019/0090735 A1* | 3/2019 | Fujii ........................ A61B 3/12 |
| 2019/0274541 A1* | 9/2019 | Higuchi .................. A61B 5/004 |
| 2021/0104313 A1* | 4/2021 | Mizobe ................ G06T 7/0012 |
| 2022/0142468 A1* | 5/2022 | Hirose ................ G06T 7/0012 |
| 2024/0008737 A1* | 1/2024 | Mabuchi .................. A61B 3/12 |

FOREIGN PATENT DOCUMENTS

| | | |
|---|---|---|
| JP | 2011-167285 A | 9/2011 |
| JP | 2012-147977 A | 8/2012 |
| JP | 2013-223 A | 1/2013 |
| JP | 2014-217745 A | 11/2014 |
| JP | 2018-139717 A | 9/2018 |

OTHER PUBLICATIONS

Office Action issued on Mar. 12, 2024, in corresponding Japanese patent Application No. 2023-130596, 6 pages.
Office Action issued on Dec. 20, 2022, in corresponding Japanese patent Application No. 2019-135240, 8 pages.

* cited by examiner

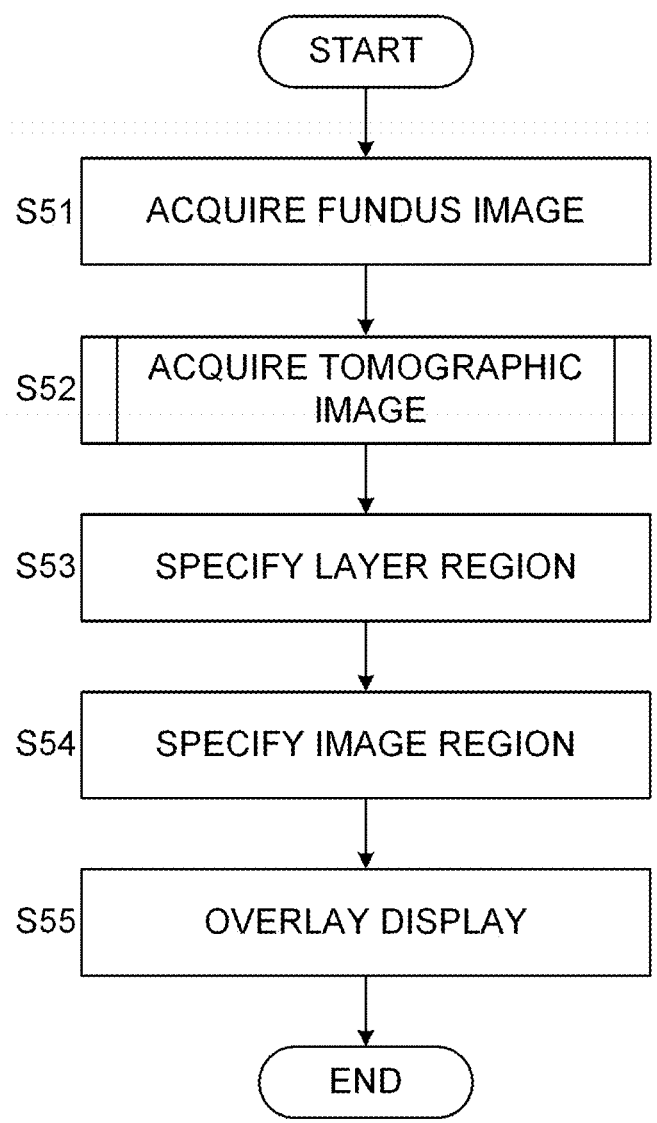

OPHTHALMOLOGICAL INFORMATION PROCESSING APPARATUS, OPHTHALMOLOGICAL APPARATUS, OPHTHALMOLOGICAL INFORMATION PROCESSING METHOD, AND RECORDING MEDIUM

CROSS-REFERENCE TO RELATED APPLICATIONS

The present application is a continuation application of International Patent Application No. PCT/JP2020/020478, filed May 25, 2020, which claims priority to Japanese Patent Application No. 2019-135240, filed Jul. 23, 2019. The contents of these applications are incorporated herein by reference in their entirety.

FIELD

The disclosure relates to an ophthalmological information processing apparatus, an ophthalmological apparatus, an ophthalmological information processing method, and a recording medium.

BACKGROUND

In recent years, attention has been drawn to optical coherence tomography (OCT) which is used to form images representing the surface morphology or the internal morphology of an object to be measured using light beam emitted from a laser light source or the like. Since OCT does not have invasiveness to human body as X-ray CT (Computed Tomography) does, development of application of OCT in medical field and biology field is particularly expected. For example, in the ophthalmological field, apparatuses for forming images of the fundus, the cornea, or the like have been in practical use. Such an apparatus using OCT imaging (OCT apparatus) can be used to observe a variety of sites of a subject's eye. In addition, the OCT apparatuses are applied to the diagnosis of various eye diseases.

In case of performing OCT measurement on a predetermined site inside the subject's eye, the measurement light for scanning the predetermined site is made incident on the eye from the pupil, and the measurement light is deflected, for example, around the scan center position arranged near the pupil. For example, A-scan images are formed from acquired A-scan data, and a tomographic image (B-scan image) is obtained by arranging a plurality of A-scan images in a B-scan direction (for example, Japanese Unexamined Patent Application Publication No. 2011-167285).

SUMMARY

One aspect of some embodiments is an ophthalmological information processing apparatus, including: an acquisition unit configured to acquire a front image depicting a predetermined site of a subject's eye in multiple gradations and an OCT image of the subject's eye; and an image correcting unit configured to correct a pixel value in a region including a first position of the predetermined site in the OCT image based on a pixel value at a second position corresponding to the first position in the front image.

Another aspect of some embodiments is an ophthalmological information processing apparatus, including: an acquisition unit configured to acquire a front image depicting a predetermined site of a subject's eye in multiple gradations and an OCT image of the subjects eye; and a display controller configured to display a region including a first position in the predetermined site in the OCT image on a display means, based on a pixel value at a second position corresponding to the first position in the front image.

Still another aspect of some embodiments is an ophthalmological apparatus, including: an imaging unit configured to image the predetermined site; an OCT unit configured to acquire the OCT image; and the ophthalmological information processing apparatus of any of the above.

Still another aspect of some embodiments is an ophthalmological information processing method, including: an acquisition step of acquiring a front image depicting a predetermined site of a subject's eye in multiple gradations and an OCT image of the subject's eye; and an image correcting step of correcting a pixel value in a region including a first position of the predetermined site in the OCT image based on a pixel value at a second position corresponding to the first position in the front image.

Still another aspect of some embodiments is an ophthalmological information processing method, including: an acquisition step of acquiring a front image depicting a predetermined site of a subject's eye in multiple gradations and an OCT image of the subject's eye; and a display control step of displaying a region including a first position in the predetermined site in the OCT image on a display means, based on a pixel value at a second position corresponding to the first position in the front image.

Still another aspect of some embodiments is a non-transitory computer readable recording medium storing a program of causing a computer to execute each step of the ophthalmological information processing method of any on the above.

BRIEF DESCRIPTION OF THE DRAWINGS

FIG. 18 is a schematic diagram illustrating an example of an operation of the ophthalmological apparatus according to the embodiments.

DETAILED DESCRIPTION

Figure 1:
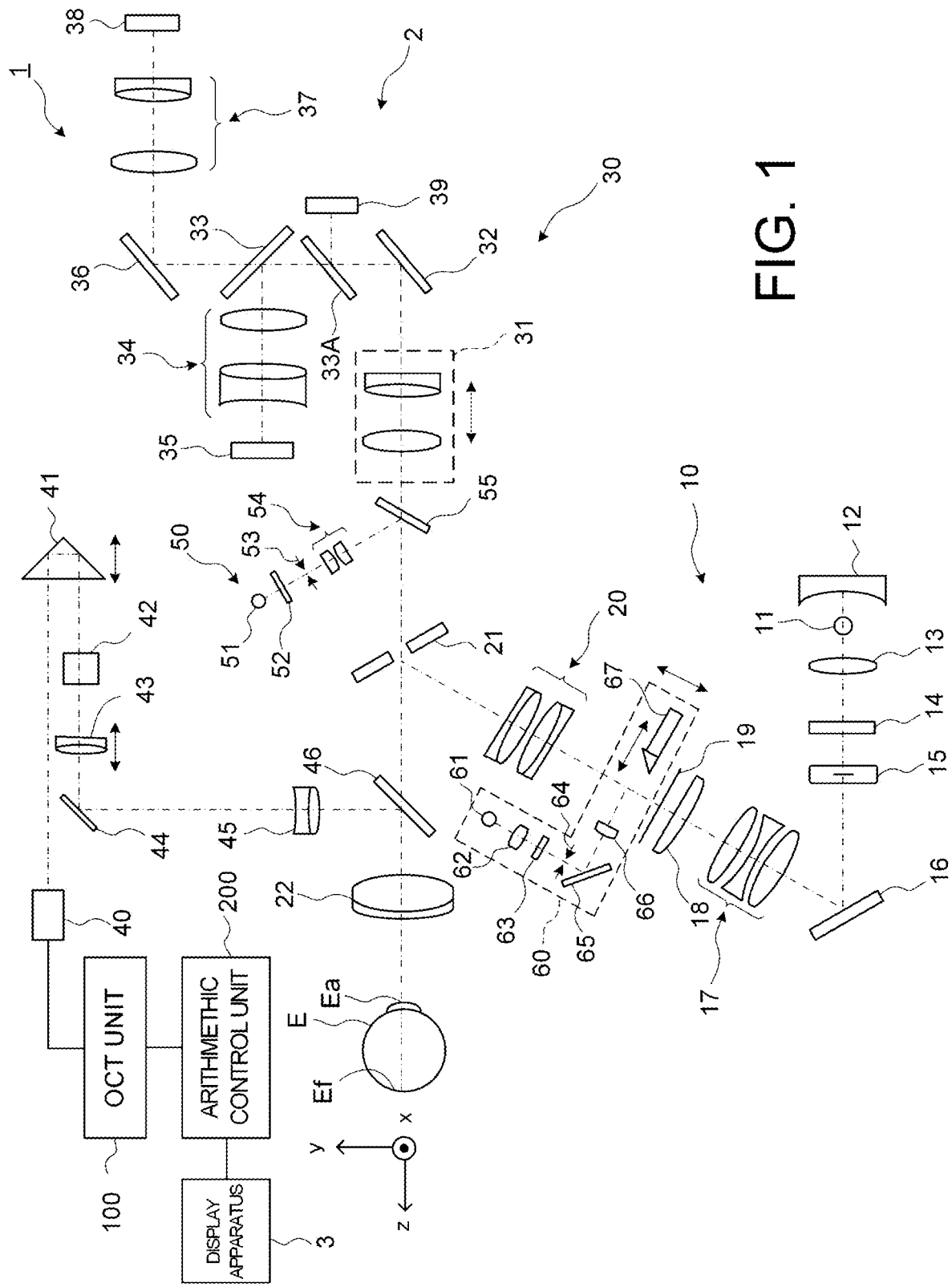
FIG. 1 is a schematic diagram illustrating an example of a configuration of an ophthalmological apparatus according to embodiments.

In general, the image quality of OCT images of the subject's eye acquired using OCT is lower than that of front images using a fundus camera, etc. Thus, doctors, etc. find it difficult to grasp the morphology of the fundus, etc. in detail using OCT images alone.

According to some embodiments of the present invention, a new technique for grasping a morphology of a predetermined site of a subject's eye from an image acquired OCT can be provided.

Referring now to the drawings, exemplary embodiments of an ophthalmological information processing apparatus, an ophthalmological apparatus, an ophthalmological information processing method, and a program according to the present invention are described below. Any of the contents of the documents cited in the present specification and arbitrary known techniques may be applied to the embodiments below.

An ophthalmological information processing apparatus according to embodiments is configured to acquire a front image depicting a predetermined site of a subjects eye in multiple gradations and an OCT image of the subject's eye obtained by performing OCT on the predetermined site. The ophthalmological information processing apparatus can display a region including a first position (first pixel position) in the predetermined site in the OCT image on a display means, based on a pixel value at a second position (second pixel position) corresponding to the first position in the front image. In some embodiments, the ophthalmological information processing apparatus corrects a pixel value (pixel values) in a region including the first position in the predetermined site in the OCT image, based on a pixel value at the second position in the front image. In some embodiments, the ophthalmological information processing apparatus displays a corrected OCT image (correction OCT image) on the display means.

In some embodiments, the front image is a two-dimensional color image or a two-dimensional grayscale image. Here, in the color image, each pixel has a grayscale value (broadly speaking, a pixel value) that corresponds to a grayscale level for each of two or more color components. In the grayscale image, each pixel has a grayscale value (broadly speaking, a pixel value) that represents a grayscale (shading). In some embodiments, the front image is acquired using a fundus camera or a scanning laser ophthalmoscope. In some embodiments, the OCT image is a two-dimensional or a three-dimensional image.

In some embodiments, the predetermined site is an anterior segment or a posterior segment. Examples of the anterior segment include a cornea, an iris, a crystalline lens, a ciliary body, and a ciliary zonule. Examples of the posterior segment include a vitreous body, and a fundus or the vicinity of the fundus (retina, choroid, sclera, etc.).

In some embodiments, the grayscale representation of the front image described above is applied to the acquired OCT image. In some embodiments, the grayscale representation of the front image is applied to the OCT image by overlay at least a part of the front image described above (a region in the front image corresponding to an image region in the OCT image) on the image region in the acquired OCT image. In some embodiments, the correction OCT image is generated by correcting a shape of the predetermined site along a traveling direction of measurement light for performing OCT on the acquired OCT image, and the grayscale representation of the front image described above is applied to the generated correction OCT image.

According to a method described above, the grayscale representation of a high quality front image can be applied to an OCT image with lower quality than the front image. This allows to easily grasp the morphology of the predetermined site in the subject's eye using the OCT image.

An ophthalmological information processing method according to the embodiments includes one or more steps for realizing the processing executed by a processor (computer) in the ophthalmological information processing apparatus according to the embodiments. A program according to the embodiments causes the processor to execute each step of the ophthalmological information processing method according to the embodiments.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

In this specification, an image acquired using OCT may be collectively referred to as an "OCT image". Also, the measurement operation for forming OCT images may be referred to as OCT measurement.

Hereinafter, the case where the ophthalmological apparatus according to the embodiments has the function of the ophthalmological information processing apparatus according to the embodiments will be described. However, the ophthalmological information processing apparatus according to the embodiments may be configured to acquire at least one of the tomographic image and the front image from an external ophthalmological apparatus. Further, the ophthalmological information processing apparatus may be configured to acquire scan data obtained by performing OCT measurement and to form the OCT image from the acquired scan data.

Hereinafter, in the embodiments, the case of using the swept source type OCT method in the measurement or the imaging (photographing) using OCT will be described. However, the configuration according to the embodiments can also be applied to an ophthalmological apparatus using other type of OCT (for example, spectral domain type OCT or time domain OCT).

The ophthalmological apparatus according to some embodiments includes any one or more of an ophthalmological imaging apparatus, an ophthalmological measuring apparatus, and an ophthalmological therapy apparatus. The ophthalmological imaging apparatus included in the ophthalmological apparatus according to some embodiments includes, for example, any one or more of a fundus camera, a scanning laser ophthalmoscope, a slit lamp ophthalmoscope, a surgical microscope, and the like. Further, the ophthalmological measuring apparatus included in the ophthalmological apparatus according to some embodiments includes any one or more of an eye refractivity examination apparatus, a tonometer, a specular microscope, a wave-front analyzer, a perimeter, a microperimeter, and the like, for example. Further, the ophthalmological therapy apparatus included in the ophthalmological apparatus according to some embodiments includes any one or more of a laser therapy apparatus, a surgical apparatus, a surgical microscope, and the like, for example.

The ophthalmological apparatus according to the following embodiments includes an OCT apparatus and a fundus camera. The OCT apparatus can perform OCT measurement.

Hereinafter, an ophthalmological apparatus capable of performing OCT measurement on a fundus of the subject's eye will be described as an example. However, the ophthalmological apparatus according to the embodiments may be capable of performing OCT measurement on an anterior segment of the subject's eye. In some embodiments, a measurement site of the OCT measurement and/or a range of the OCT measurement are/is changed by moving a lens for changing focal position of measurement light. In some embodiments, the ophthalmological apparatus has a configuration capable of performing OCT measurement on the fundus, OCT measurement on the anterior segment, and OCT measurement on the whole eyeball including the fundus and anterior segment, by adding one or more attachments (objective lens, front lens, etc.). In some embodiments, in the ophthalmological apparatus for measuring fundus, OCT measurement is performed on the anterior segment, by making the measurement light incident on the subject's eye, the measurement light having been converted into a parallel light flux by arranging a front lens between the objective lens and the subject's eye.

First Embodiment

In a first embodiment, a pixel value in a region of at least a part of the fundus depicted in the OCT image of the subject's eye is corrected using a pixel value in a region corresponding to the region in the color (or grayscale) front image of the fundus, and the corrected OCT image is displayed on a display means.

Configuration

Optical System

As shown in FIG. 1, the ophthalmological apparatus 1 includes a fundus camera unit 2, an OCT unit 100, and an arithmetic control unit 200. The fundus camera unit 2 is provided with an optical system and a mechanism for acquiring front images of a subject's eye E. The OCT unit 100 is provided with a part of an optical system and a mechanism for performing OCT. Another part of the optical system and the mechanism for performing OCT are provided in the fundus camera unit 2. The arithmetic control unit 200 includes one or more processors for performing various kinds of arithmetic processing and control processing. In addition to these elements, an arbitrary element or a unit, such as a member (chin rest, forehead pad, etc.) for supporting a face of the subject, a lens unit (for example, an attachment for an anterior segment OCT) for switching the target site of OCT, and the like, may be provided in the ophthalmological apparatus 1. In some embodiments, the lens unit is configured to be manually inserted and removed between the subject's eye E and an objective lens 22 described below. In some embodiments, the lens unit is configured to be automatically inserted and removed between the subject's eye E and the objective lens 22 described below, under the control of the controller 210 described below.

In some embodiments, the ophthalmological apparatus 1 includes a display apparatus 3. The display apparatus 3 displays a processing result (for example, an OCT image or the like) obtained by the arithmetic control unit 200, an image obtained by the fundus camera unit 2, operation guidance information for operating the ophthalmological apparatus 1, and the like.

Fundus Camera Unit

The fundus camera unit 2 is provided with an optical system for imaging (photographing) a fundus Ef of the subject's eye E. An image (called fundus image, fundus photograph, etc.) of the fundus Ef to be obtained is a front image such as an observation image, a photographic image, or the like. The observation image is obtained by moving image shooting using near infrared light. The photographic image is a color still image using flash light. Furthermore, the fundus camera unit 2 can obtain the front image (anterior segment image) by photographing (imaging) an anterior segment Ea of the subject's eye E.

The fundus camera unit 2 includes an illumination optical system 10 and an imaging (photographing) optical system 30. The illumination optical system 10 projects illumination light onto the subject's eye E. The imaging optical system 30 detects returning light of the illumination light from the subject's eye E. Measurement light from the OCT unit 100 is guided to the subject's eye E through an optical path in the fundus camera unit 2. Returning light of the measurement light is guided to the OCT unit 100 through the same optical path.

Light (observation illumination light) emitted from the observation light source 11 of the illumination optical system 10 is reflected by a reflective mirror 12 having a curved reflective surface, and becomes near-infrared light after being transmitted through a visible cut filter 14 via a condenser lens 13. Further, the observation illumination light is once converged near an imaging light source 15, is reflected by a mirror 16, and passes through relay lenses 17 and 18, a diaphragm 19, and a relay lens 20. Then, the observation illumination light is reflected on the peripheral part (the surrounding area of a hole part) of a perforated mirror 21, is transmitted through a dichroic mirror 46, and is refracted by the objective lens 22, thereby illuminating the subject's eye E (fundus Ef or anterior segment Ea). Returning light of the observation illumination light reflected from the subject's eye E is refracted by the objective lens 22, is transmitted through the dichroic mirror 46, passes through the hole part formed in the center region of the perforated mirror 21, is transmitted through a dichroic mirror 55. The returning light transmitted through the dichroic mirror 55 travels through a photography focusing lens 31 and is reflected by a mirror 32. Further, this returning light is transmitted through a half mirror 33A, is reflected by a dichroic mirror 33, and forms an image on the light receiving surface of an image sensor 35 by a condenser lens 34. The image sensor 35 detects the returning light at a predetermined frame rate. It should be noted that the focus of the imaging optical system 30 is adjusted so as to coincide with the fundus Ef or the anterior segment Ea.

Light (imaging illumination light) emitted from the imaging light source 15 is projected onto the fundus Ef via the same route as that of the observation illumination light. Returning light of the imaging illumination light from the subject's eye E is guided to the dichroic mirror 33 via the same route as that of the observation illumination light, is transmitted through the dichroic mirror 33, is reflected by a mirror 36, and forms an image on the light receiving surface of the image sensor 38 by a condenser lens 37.

A liquid crystal display (LCD) 39 displays a fixation target and a visual target used for visual acuity measurement. Part of light output from the LCD 39 is reflected by the half mirror 33A, is reflected by the mirror 32, travels through the photography focusing lens 31 and the dichroic mirror 55, and passes through the hole part of the perforated mirror 21. The light flux (beam) having passed through the hole part of the perforated mirror 21 is transmitted through the dichroic mirror 46, and is refracted by the objective lens 22, thereby being projected onto the fundus Ef.

By changing the display position of the fixation target on the screen of the LCD 39, the fixation position of the subject's eye E can be changed. Examples of the fixation position include a fixation position for acquiring an image centered at a macula, a fixation position for acquiring an image centered at an optic disc, a fixation position for acquiring an image centered at a fundus center between the macula and the optic disc, a fixation position for acquiring an image of a site (fundus peripheral part) far away from the macula, and the like. The ophthalmological apparatus 1 according to some embodiments includes GUI (Graphical User Interface) and the like for designating at least one of such fixation positions. The ophthalmological apparatus 1 according to some embodiments includes GUI etc. for manually moving the fixation position (display position of the fixation target).

The configuration for presenting the movable fixation target to the subject's eye E is not limited to the display device such LCD or the like. For example, the movable fixation target can be generated by selectively turning on a plurality of light sources of a light source array (light emitting diode (LED) array or the like). Alternatively, the movable fixation target can be generated using one or more movable light sources.

Further, the ophthalmological apparatus 1 may be provided with one or more external fixation light sources. One of the one or more external fixation light sources can project fixation light onto a fellow eye of the subject's eye E. A projected position of the fixation light on the fellow eye can be changed. By changing the projected position of the fixation light on the fellow eye, the fixation position of the subject's eye E can be changed. The fixation position projected by the external fixation light source(s) may be the same as the fixation position of the subject's eye E using the LCD 39. For example, the movable fixation target can be generated by selectively turning on the plurality of external fixation light sources. Alternatively, the movable fixation target can be generated using one or more movable external fixation light sources.

The alignment optical system 50 generates an alignment indicator for alignment of the optical system with respect to the subject's eye E. Alignment light emitted from an LED 51 travels through the diaphragms 52 and 53 and the relay lens 54, is reflected by the dichroic mirror 55, and passes through the hole part of the perforated mirror 21. The light having passed through the hole part of the perforated mirror 21 is transmitted through the dichroic mirror 46, and is projected onto the subject's eye E by the objective lens 22. Corneal reflection light of the alignment light is guided to the image sensor 35 through the same route as the returning light of the observation illumination light. Manual alignment or automatic alignment can be performed based on the received light image (alignment indicator image) thereof.

The focus optical system 60 generates a split indicator for adjusting the focus with respect to the subject's eye E. The focus optical system 60 is movable along an optical path (illumination optical path) of the illumination optical system 10 in conjunction with the movement of the photography focusing lens 31 along an optical path (imaging optical path) of the imaging optical system 30. The reflection rod 67 can be inserted and removed into and from the illumination optical path. To perform focus adjustment, the reflective surface of the reflection rod 67 is arranged in a slanted position on the illumination optical path. Focus light emitted from an LED 61 passes through a relay lens 62, is split into two light beams by a split indicator plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the perforated mirror 21, is transmitted through the dichroic mirror 46, and is refracted by the objective lens 22, thereby being projected onto the fundus Ef. Fundus reflection light of the focus light is guided to the image sensor 35 through the same route as the corneal reflection light of the alignment light. Manual focus or automatic focus can be performed based on the received light image (split indicator image) thereof.

The dichroic mirror 46 combines an optical path for fundus photography and an optical path for OCT. The dichroic mirror 46 reflects light of wavelength band used in OCT, and transmits light for fundus imaging. The optical path for OCT (optical path of measurement light) is provided with, in order from the OCT unit 100 side to the dichroic mirror 46 side, a collimator lens unit 40, an optical path length changing unit 41, an optical scanner 42, an OCT focusing lens 43, a mirror 44, and a relay lens 45.

The optical path length changing unit 41 is movable in directions indicated by the arrow in FIG. 1, thereby changing the length of the optical path for OCT. This change in the optical path length is used for correcting the optical path length according to the axial length, adjusting the interference state, or the like. The optical path length changing unit 41 includes a corner cube and a mechanism for moving the corner cube.

The optical scanner 42 is disposed at a position optically conjugate to the pupil of the subject's eye E. The optical scanner 42 deflects the measurement light traveling along the OCT optical path. That is, the optical scanner 42 deflects the measurement light for scanning inside the subject's eye E while changing the scan angle within a predetermined deflection angle range with the pupil (or the vicinity thereof)

of the subject's eye E as the scan center position. The optical scanner 42 can deflect the measurement light in a one-dimensionally or two-dimensional manner.

In case that the optical scanner 42 deflects the measurement light in a one-dimensionally manner, the optical scanner 42 includes a galvano scanner capable of deflecting the measurement light in a predetermined deflection direction within a predetermined deflection angle range. In case that the optical scanner deflects the measurement light LS in a two-dimensionally manner, the optical scanner 42 includes a first galvano scanner and a second galvano scanner. The first galvano scanner deflects the measurement light so as to scan a photographing (imaging) site (fundus Ef or the anterior segment) in a horizontal direction orthogonal to the optical axis of the OCT optical system 8. The second galvano scanner deflects the measurement light deflected by the first galvano mirror so as to scan the photographing site in a vertical direction orthogonal to the optical axis of the OCT optical system 8. Examples of scan mode with the measurement light performed by the optical scanner 42 include horizontal scan, vertical scan, cross scan, radial scan, circle scan, concentric scan, helical (spiral) scan, and the like.

The OCT focusing lens 43 is moved along the optical path of the measurement light in order to perform focus adjustment of the optical system for OCT. The OCT focusing lens 43 can move within a moving range. The moving range includes a first lens position for placing the focal position of the measurement light at the fundus Ef or near the fundus Ef of the subject's eye E and a second lens position for making the measurement light projected onto the subject's eye E a parallel light beam. The movement of the photography focusing lens 31, the movement of the focus optical system 60, and the movement of the OCT focusing lens 43 can be controlled in conjunction with each other.

OCT Unit

Figure 2:
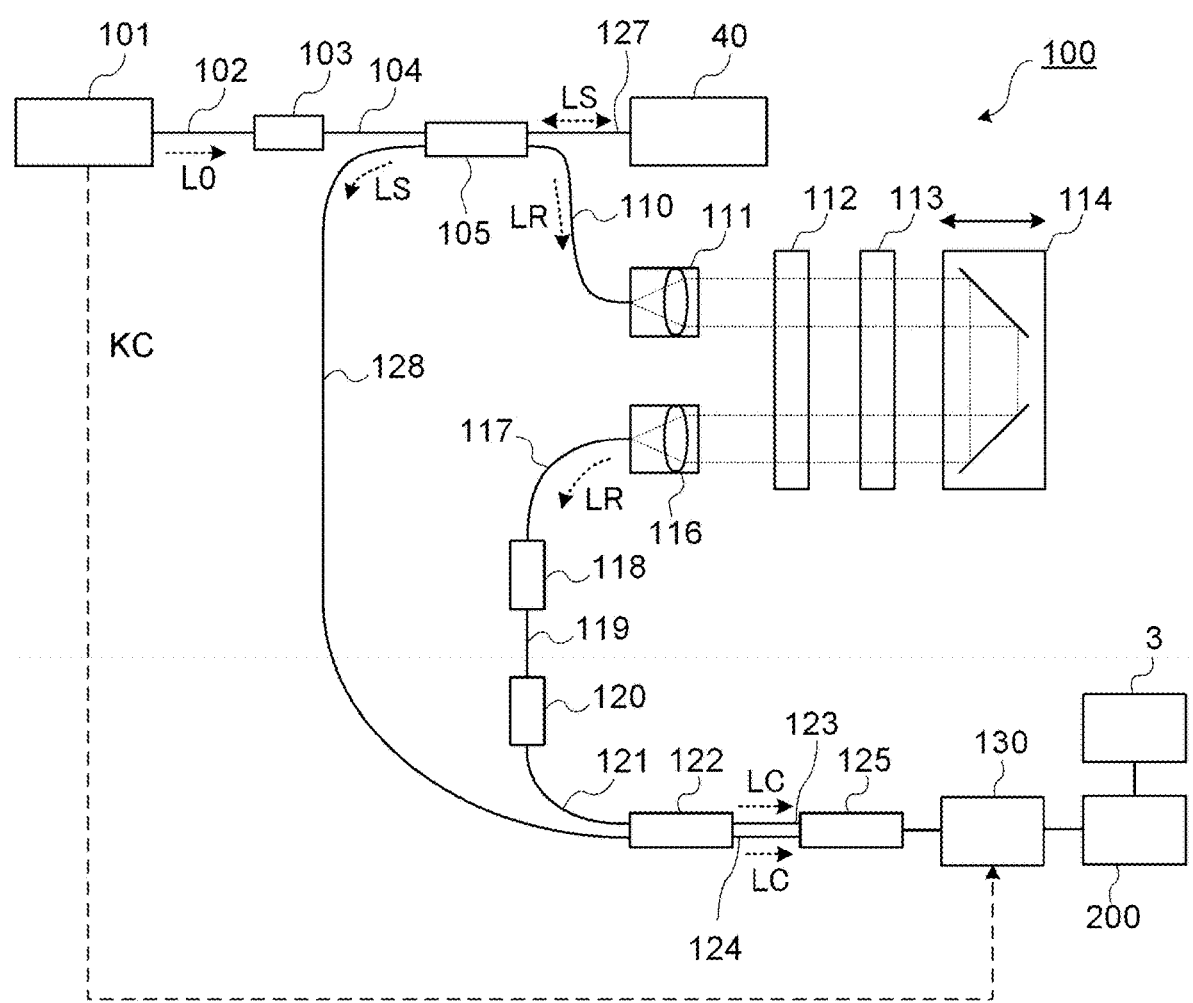
FIG. 2 is a schematic diagram illustrating an example of the configuration of an ophthalmological apparatus according to the embodiments.

An example of the configuration of the OCT unit 100 is shown in FIG. 2. The OCT unit 100 is provided with an optical system for acquiring tomographic images as OCT images of the subject's eye E. The optical system includes an interference optical system that splits light from a wavelength sweeping type (i.e., a wavelength scanning type) light source into measurement light and reference light, makes the measurement light returning from the subject's eye E and the reference light having traveled through the reference optical path interfere with each other to generate interference light, and detects the interference light. The detection result of the interference light obtained by the interference optical system (i.e., the detection signal) is an interference signal indicating the spectrum of the interference light, and is sent to the arithmetic control unit 200.

Like swept source type ophthalmological apparatuses commonly used, the light source unit 101 includes a wavelength sweeping type (i.e., a wavelength scanning type) light source capable of sweeping (scanning) the wavelengths of emitted light. The wavelength sweeping type light source includes a laser light source that includes a resonator. The light source unit 101 temporally changes the output wavelengths within the near-infrared wavelength bands that cannot be visually recognized with human eyes.

The light L0 emitted from the light source unit 101 is guided to the polarization controller 103 through the optical fiber 102, and the polarization state of the light L0 is adjusted. The polanzation controller 103, for example, applies external stress to the looped optical fiber 102 to thereby adjust the polarization state of the light L0 guided through the optical fiber 102.

The light L0 whose polarization state has been adjusted by the polarization controller 103 is guided to the fiber coupler 105 through the optical fiber 104, and is split into the measurement light LS and the reference light LR.

The reference light LR is guided to the collimator 111 through the optical fiber 110. The reference light LR is converted into a parallel light beam by the collimator 111. Then, the reference light LR is guided to the optical path length changing unit 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS.

The optical path length changing unit 114 is movable in directions indicated by the arrow in FIG. 2, thereby changing the length of the optical path of the reference light LR. Through such movement, the length of the optical path of the reference light LR is changed. The change in the optical path length is used for the correction of the optical path length according to the axial length of the subject's eye E, for the adjustment of the interference state, or the like. The optical path length changing unit 114 includes, for example, a corner cube and a movement mechanism for moving the corner cube. In this case, the corner cube in the optical path length changing unit 114 changes the traveling direction of the reference light LR that has been made into the parallel light flux by the collimator 111 in the opposite direction. The optical path of the reference light LR incident on the corner cube and the optical path of the reference light LR emitted from the corner cube are parallel.

The reference light LR that has traveled through the optical path length changing unit 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to the polarization controller 118. With the polarization controller 118, the polarized state (polarization state) of the reference light LR is adjusted. The polarization controller 118 has the same configuration as, for example, the polarization controller 103. The reference light LR whose polarization state has been adjusted by the polarization controller 118 is guided to the attenuator 120 by the optical fiber 119, and the light amount of the reference light LR is adjusted under the control of the arithmetic control unit 200. The reference light LR whose light amount has been adjusted by the attenuator 120 is guided to the fiber coupler 122 by the optical fiber 121.

The configuration shown in FIG. 1 and FIG. 2 includes both the optical path length changing unit 41 that changes the length of the optical path of the measurement light LS (i.e., measurement optical path or measurement arm) and the optical path length changing unit 114 that changes the length of the optical path of the reference light LR (i.e., reference optical path or reference arm). However, any one of the optical path length changing units 41 and 114 may be provided. The difference between the measurement optical path length and the reference optical path length can be changed by using other optical members.

Meanwhile, the measurement light LS generated by the fiber coupler 105 is guided through the optical fiber 127, and is made into the parallel light beam by the collimator lens unit 40. The measurement light LS made into the parallel light flux is guided to the dichroic mirror 46 via the optical path length changing unit 41, the optical scanner 42, the OCT focusing lens 43, the mirror 44, and the relay lens 45. The measurement light LS guided to the dichroic mirror 46 is reflected by the dichroic mirror 46, refracted by the objective lens 22, and projected onto the subject's eye E. The measurement light LS is scattered (and reflected) at various depth positions of the subject's eye E. The returning light of the measurement light LS including such backscattered light advances through the same path as the outward path in the opposite direction and is led to the fiber coupler 105, and then reaches the fiber coupler 122 through the optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 is guided to the detector 125 through the optical fibers 123 and 124, respectively.

The detector 125 is, for example, a balanced photodiode that includes a pair of photodetectors for respectively detecting the pair of interference light LC and outputs the difference between the pair of detection results obtained by the pair of photodetectors. The detector 125 sends the detection result (i.e., interference signal) to the data acquisition system (DAQ) 130. A clock KC is supplied from the light source unit 101 to the DAQ 130. The clock KC is generated in the light source unit 101 in synchronization with the output timing of each wavelength sweeping (scanning) within a predetermined wavelength range performed by the wavelength sweeping type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs sampling of the detection result obtained by the detector 125 based on the clock KC. The DAQ 130 sends the result of the sampling of the detection result obtained by the detector 125 to the arithmetic control unit 200. For example, the arithmetic control unit 200 performs the Fourier transform etc. on the spectral distribution based on the detection result obtained by the detector 125 for each series of wavelength scanning (i.e., for each A-line). With this, the reflection intensity profile for each A-line is formed. In addition, the arithmetic control unit 200 forms image data by applying imaging processing to the reflection intensity profiles for the respective A-lines.

Arithmetic Control Unit

The arithmetic control unit 200 analyzes the detection signals fed from the DAQ 130 to form an OCT image or scan data of the fundus Ef (or the anterior segment Ea). The arithmetic processing therefor is performed in the same manner as in the conventional swept-source-type OCT apparatus.

Further, the arithmetic control unit 200 controls each part of the fundus camera unit 2, the display apparatus 3, and the OCT unit 100.

Also, as the control of the fundus camera unit 2, the arithmetic control unit 200 performs following controls: the operation control of the observation light source 11, the operation control of the imaging light source 15 and the operation control of the LEDs 51 and 61; the operation control of the LCD 39; the movement control of the photography focusing lens 31; the movement control of the OCT focusing lens 43; the movement control of the reflection rod 67, the movement control of the focus optical system 60; the movement control of the optical path length changing unit 41; the operation control of the optical scanner 42, and the like.

As the control of the display apparatus 3, the arithmetic control unit 200 controls the display apparatus 3 to display the OCT image of the subject's eye E.

As the control of the OCT unit 100, the arithmetic control unit 200 controls: the operation of the light source unit 101; the operation of the optical path length changing unit 114; the operations of the attenuator 120; the operation of the polarization controllers 103 and 118; the operation of the detector 125; the operation of the DAQ 130; and the like.

As in the conventional computer, the arithmetic control unit 200 includes a processor, random access memory (RAM), read only memory (ROM), hard disk drive, and communication interface, for example. A storage device such as the hard disk drive stores a computer program for controlling the ophthalmological apparatus 1. The arithmetic control unit 200 may include various kinds of circuitry such as a circuit board for forming OCT images. In addition, the arithmetic control unit 200 may include an operation device (or an input device) such as a keyboard and a mouse, and a display device such as an LCD.

The fundus camera unit 2, the display apparatus 3, the OCT unit 100, and the arithmetic control unit 200 may be integrally provided (i.e., in a single housing), or they may be separately provided in two or more housings.

Control System

Figure 3:
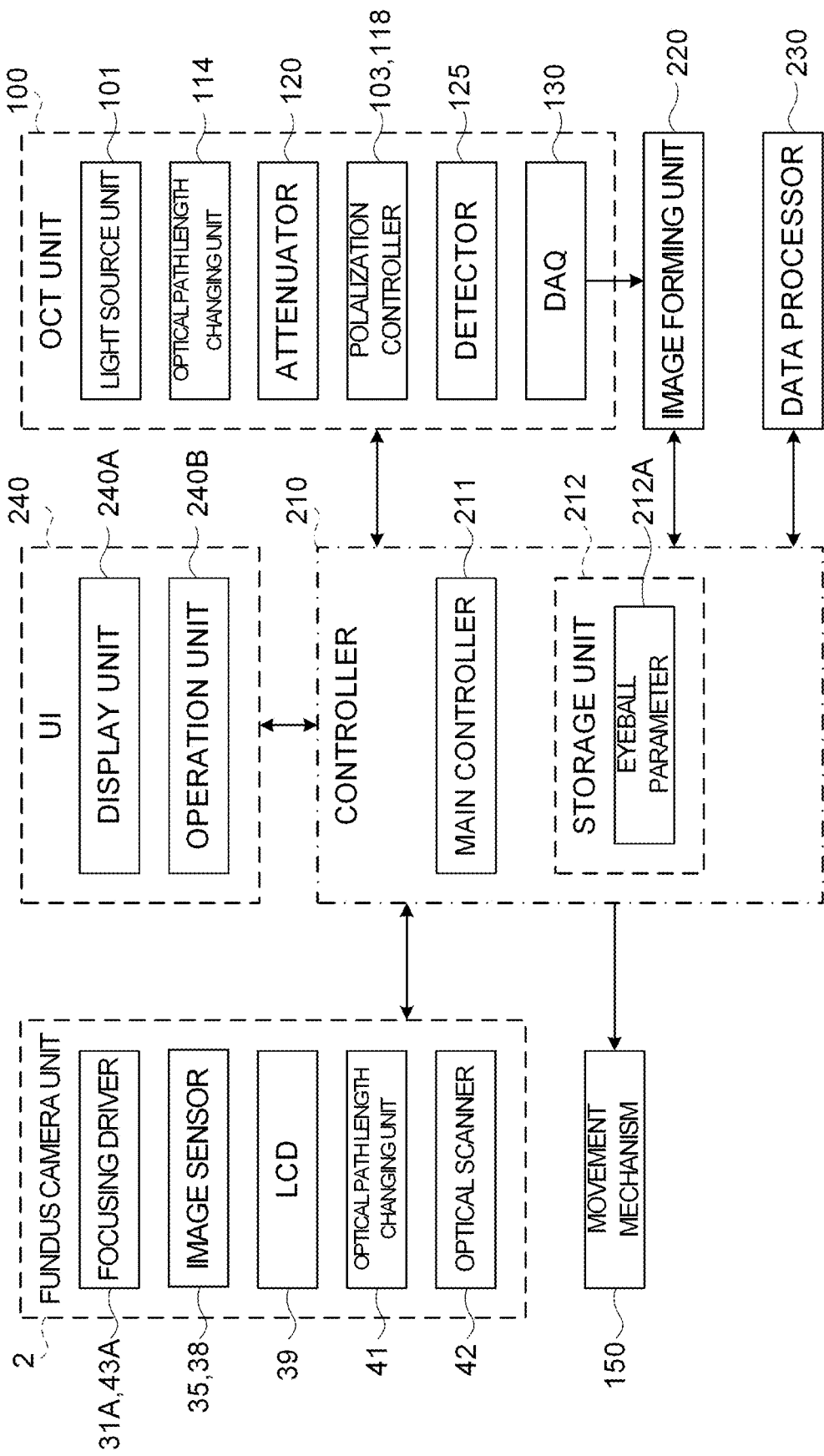
FIG. 3 is a schematic block diagram illustrating an example of a configuration of the ophthalmological apparatus according to the embodiments.
Figure 4:
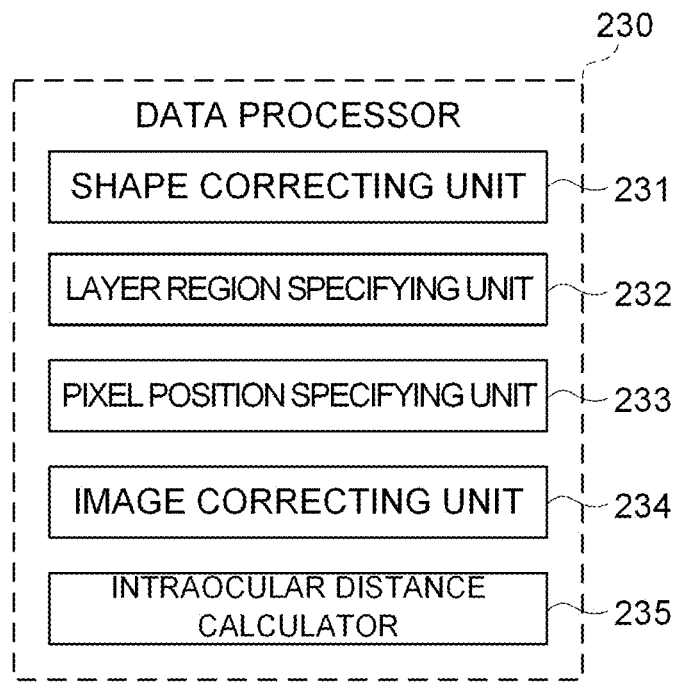
FIG. 4 is a schematic block diagram illustrating an example of the configuration of the ophthalmological apparatus according to the embodiments.
Figure 5:
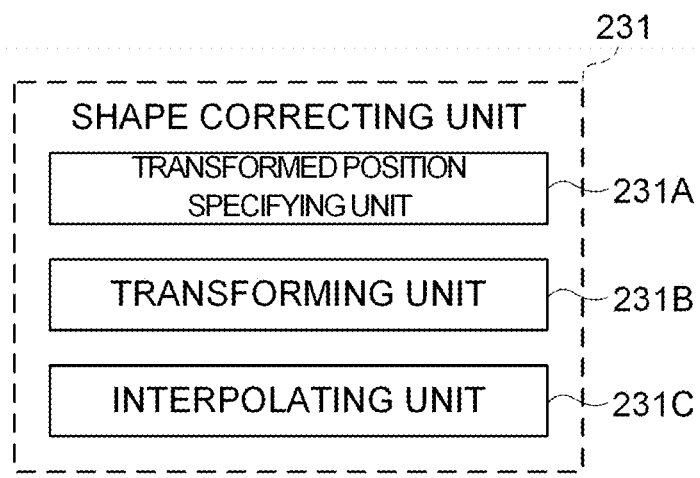
FIG. 5 is a schematic block diagram illustrating an example of the configuration of the ophthalmological apparatus according to the embodiments.

FIGS. 3 to 5 illustrate configuration examples of a control system of the ophthalmological apparatus 1. In FIGS. 3 to 5, a part of the components included in the ophthalmological apparatus 1 is omitted.

The arithmetic control unit 200 includes a controller 210.

Controller

The controller 210 executes various controls. The controller 210 includes a main controller 211 and a storage unit 212.

Main Controller

The main controller 211 includes a processor and controls each part of the ophthalmological apparatus 1. For example, the main controller 211 controls components of the fundus camera unit 2 such as focusing drivers 31A and 43A, the image sensors 35 and 38, the LCD 39, the optical path length changing unit 41, the optical scanner 42, and a movement mechanism 150 for moving the optical system. Further, the main controller 211 controls components of the OCT unit 100 such as the light source unit 101, the optical path length changing unit 114, the attenuator 120, the polarization controllers 103 and 118, the detector 125, and the DAQ 130.

For example, the main controller 211 controls the LCD 39 to display the fixation target at a position on the screen of the LCD 39 corresponding the fixation position set manually or automatically. Moreover, the main controller 211 can change the display position of the fixation target displayed on the LCD 39 (in a continuous manner or in a phased manner). Thereby, the fixation target can be moved (that is, the fixation position can be changed). The display position of the fixation target and movement mode of the fixation target are set manually or automatically. Manual setting is performed using GUI, for example. Automatic setting is performed by the data processor 230, for example.

The focusing driver 31A moves the photography focusing lens 31 in the direction along the optical axis of the imaging optical system 30, and moves the focus optical system 60 in the direction along the optical axis of the illumination optical system 10. With this, the focus position of the imaging optical system 30 is changed. The focusing driver 31A may include a dedicated mechanism for moving the photography focusing lens 31 and a dedicated mechanism for moving the focus optical system 60. The focusing driver 31A is controlled when performing focus adjustment or the like.

The focusing driver 43A moves the OCT focusing lens 43 in the optical axis direction of the measurement optical path. As a result, the focusing position of the measurement light LS is changed. For example, the focus position of the measurement light LS can be arranged at the fundus Ef or near the fundus Ef by moving the OCT focusing lens 43 to the first lens position. For example, the focus position of the measurement light LS can be arranged at a far point position by moving the OCT focusing lens 43 to the second lens position. The focus position of the measurement light LS corresponds to the depth position (z position) of the beam waist of the measurement light LS.

The movement mechanism 150 three-dimensionally moves at least the fundus camera unit 2 (optical system), for example. In a typical example, the movement mechanism 150 includes a mechanism for moving at least the fundus camera unit 2 in the x direction (left-right direction), a mechanism for moving it in the y direction (up-down direction), and a mechanism for moving it in the z direction (depth direction, front-back direction). The mechanism for moving in the x direction includes ax stage movable in the x direction and a x movement mechanism for moving the x stage, for example. The mechanism for moving in the y direction includes a y stage movable in the y direction and a y movement mechanism for moving the y stage, for example. The mechanism for moving in the z direction includes a z stage movable in the z direction and a z movement mechanism for moving the z stage, for example. Each movement mechanism includes an actuator such as a pulse motor, and operates under the control of the main controller 211.

The control for the movement mechanism 150 is used for alignment and tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement. In some embodiments, the movement mechanism 150 is configured to be controlled to change the optical path length of the reference light (that is, the difference of the optical path length between the optical path of the measurement light and the optical path of the reference light).

In the case of manual alignment, a user operates a user interface (UI) 240 described below to relatively move the optical system and subject's eye E so as to cancel the displacement of the subject's eye E with respect to the optical system. For example, the main controller 211 controls the movement mechanism 150 to relatively move the optical system and the subject's eye E by outputting a control signal corresponding to the operation content with respect to the user interface 240 to the movement mechanism 150.

In the case of automatic alignment, the main controller 211 controls the movement mechanism 150 to relatively move the optical system and the subject's eye E so as to cancel the displacement of the subject's eye E with respect to the optical system. In some embodiments, the main controller 211 controls the movement mechanism 150 to relatively move the optical system and the subject's eye E by outputting a control signal to the movement mechanism 150 so that the optical axis of the optical system substantially coincides with the axis of the subject's eye E and the distance of the optical system with respect to the subject's eye E is a predetermined working distance. Here, the working distance is a preset value which is called a working distance of the objective lens 22, and it means the distance between the subject's eye E and the optical system when measuring (imaging) using the optical system.

The main controller 211 controls the fundus camera unit 2 etc. to control the fundus imaging (photography) and the anterior segment imaging. Further, the main controller 211 controls the fundus camera unit 2 and the OCT unit 100 etc. to control the OCT measurement. The main controller 211 is capable of performing a plurality of preliminary operations prior to OCT measurement. Examples of the preliminary operation include alignment, rough focus adjustment, polarization adjustment, and fine focus adjustment. The plurality of preliminary operations is performed in a predetermined order. In some embodiments, the plurality of preliminary operations is performed in an order described above.

It should be noted that the types and the orders of the preliminary operations are not so limited, and they may be optional. For example, the preliminary operations may further include small-pupil judgment. The small-pupil judgment is a preliminary operation to judge whether the pupil of the subject's eye E is small or not (whether the subject's eye E is microcoria or not). The small-pupil judgment may be performed between the rough focus adjustment and the optical path length difference adjustment. In some embodiments, the small-pupil judgment includes, for example, a series of processes as follows: acquiring a front image (anterior segment image) of the subject's eye E; specifying an image region corresponding to the pupil; calculating the size (e.g., diameter, circumference length) of the pupil region; judging whether the pupil of the subject's eye E is small or not based on the calculated size (threshold processing); and controlling the diaphragm 19 when judged that the pupil of the subject's eye E is small. In some embodiments, the calculation of the size of the pupil region includes processing of circularly or elliptically approximating the pupil region.

The rough focus adjustment is a kind of focus adjustment using the split indicator. The rough focus adjustment may be performed by determining the position of the photography focusing lens 31 based on information, which is obtained by associating the eye refractive power acquired in advance with the position of the photography focusing lens 31, and a measured value of the refractive power of the subject's eye E.

The fine focus adjustment is performed on the basis of interference sensitivity of OCT measurement. For example, the fine focus adjustment can be performed by: monitoring interference intensity (interference sensitivity) of interference signal acquired by performing OCT measurement of the subject's eye E; searching the position of the OCT focusing lens 43 so as to maximize the interference intensity; and moving the OCT focusing lens 43 to the searched position.

To perform the optical path length difference adjustment, the optical system is controlled so that a predetermined position on the subject's eye E is a reference position of a measurement range in the depth direction. The control is performed on at least one of the optical path length changing units 41 and 114. Thereby, the difference of the optical path length between the measurement optical path and the reference optical path is adjusted. By setting the reference position in the optical path length difference adjustment, OCT measurement can be performed with high accuracy over a desired measurement range in the depth direction simply by changing the wavelength sweep speed.

To perform the polarization adjustment, the polarization state of the reference light LR is adjusted for optimizing the interference efficiency between the measurement light LS and the reference light LR.

(Storage Unit)

The storage unit 212 stores various types of data. Examples of the data stored in the storage unit 212 include image data of an OCT image, image data of a fundus image, scan data, image data of an anterior segment image, and subject's eye information. The subject's eye information includes information on the subject such as patient ID and name, and information on the subject's eye such as identification information of the left eye t right eye.

Further, the storage unit 212 stores an eyeball parameter 212A. The eyeball parameter 212A includes a parameter (standard value) defined by a known eyeball model such as a Gullstrand schematic eye. In some embodiments, the eyeball parameter 212A includes a parameter in which at least one of the parameters defined by a known eyeball model is replaced with the measured value of the subject's eye E. In this case, it means that the eyeball parameter 212A includes a parameter representing optical characteristics of the subject's eye E. Examples of the measured value include an axial length, a corneal thickness, a curvature radius of an anterior surface of cornea, a curvature radius of a posterior surface of cornea, an anterior chamber depth, a curvature radius of an anterior surface of a lens, a lens thickness, a curvature radius of a posterior surface of lens, a vitreous cavity length, a retinal thickness, and a choroid thickness. In some embodiments, the measured value is acquired by analyzing OCT data obtained by performing OCT measurement. The eyeball parameter 212A may include a parameter designated using the operation unit 240B described later.

In addition, the storage unit 212 stores various kinds of computer programs and data for operating the ophthalmological apparatus 1.

(Image Forming Unit)

The image forming unit 220 performs signal processing such as the Fourier transform on sampling data obtained by sampling the detection signal from the detector 125 in the DAQ 130. With this, the reflection intensity profile for each A-line is formed. The above signal processing includes noise removal (noise reduction), filtering, fast Fourier transform (FFT), and the like. The reflection intensity profile for the A-line is an example of the A-scan data. The image forming unit 220 can form the reflection intensity profile for each A-line, and form B-scan data (two-dimensional scan data) by arranging a formed plurality of reflection intensity profiles in the B-scan direction (intersecting direction of the A-scan direction).

In some embodiments, the image forming unit 220 (or data processor 230 described below) forms three-dimensional scan data by arranging the plurality of reflection intensity profiles formed for each A-line in the B-scan direction (for example, x direction) and a direction intersecting both of the A-scan direction and the B-scan direction (for example, y direction).

Further, the image forming unit 220 can form A-scan image (OCT image, image data) of the subject's eye E, by applying imaging processing to the reflection intensity profile in the A-line. The image forming unit 220 can form a B-scan image by arranging the plurality of A-scan images formed for each A-line in the B-scan direction (intersecting direction of the A-scan direction).

In some embodiments, the image forming unit 220 extracts data at a predetermined depth position (scan position) in each A-scan data, and forms C-scan data by arranging the extracted plurality of data in the B-scan direction (intersecting direction of the A-scan direction). In some embodiments, the image forming unit 220 extracts a pixel at a predetermined depth position (scan position) in each A-scan image, and forms a C-scan image by arranging the extracted plurality of pixels in the B-scan direction (intersecting direction of the A-scan direction).

In some embodiments, the function of the image forming unit 220 is realized by a processor. It should be noted that "image data" and an "image" based on the image data may not be distinguished from each other in the present specification.

Data Processor

The data processor 230 processes data acquired through photography of the subject's eye E or data acquired through OCT measurement.

For example, the data processor 230 performs various kinds of image processing and various kinds of analysis processing on the image formed by the image forming unit 220. For example, the data processor 230 performs various types of image correction processing such as brightness correction. The data processor 230 performs various kinds of image processing and various kinds of analysis processing on images captured by the fundus camera unit 2 (e.g., fundus images, anterior segment images, etc.).

The data processor 230 performs known image processing such as interpolation for interpolating pixels in tomographic images to form three-dimensional image data of the fundus Ef. Note that image data of the three-dimensional image means image data in which the positions of pixels are defined by a three-dimensional coordinate system. Examples of the image data of the three-dimensional image include image data defined by voxels three-dimensionally arranged. Such image data is referred to as volume data or voxel data. When displaying an image based on volume data, the data processor 230 performs rendering (volume rendering, maximum intensity projection (MIP), etc.) on the volume data, thereby forming image data of a pseudo three-dimensional image viewed from a particular line of sight. The pseudo three-dimensional image is displayed on the display device such as a display unit 240A.

The three-dimensional image data may be stack data of a plurality of tomographic images. The stack data is image data formed by three-dimensionally arranging tomographic images along a plurality of scan lines based on positional relationship of the scan lines. That is, the stack data is image data formed by representing tomographic images, which are originally defined in their respective two-dimensional coordinate systems, by a single three-dimensional coordinate system. That is, the stack data is image data formed by embedding tomographic images into a single three-dimensional space.

The data processor 230 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired three-dimensional data set (volume data, stack data, etc.). An image in an arbitrary cross section such as a B-mode image or a C-mode image is formed by selecting pixels (voxels) on a designated cross section from the three-dimensional data set. The projection image is formed by projecting the three-dimensional data set in a predetermined direction (z direction, depth direction, axial direction). The shadowgram is formed by projecting a part of the three-dimensional data set in a predetermined direction. Examples of the part of the three-dimensional data set include partial data corresponding to a specific layer. An image having a viewpoint on the front side of the subject's eye, such as the C-mode image, the projection image, and the shadowgram, is called a front image (en-face image).

The data processor 230 can build (form) the B-mode image or the front image (blood vessel emphasized image, angiogram) in which retinal blood vessels and choroidal blood vessels are emphasized (highlighted), based on data (for example, B-scan image data) acquired in time series by OCT. For example, the OCT data in time series can be acquired by repeatedly scanning substantially the same site of the subject's eye E.

In some embodiments, the data processor 230 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 230 forms an OCTA image by extracting information of a predetermined thickness at a desired site from a plurality of built emphasized images and building as an en-face image.

An image (for example, a three-dimensional image, a B-mode image, a C-mode image, a projection image, a shadowgram, and an OCTA image) generated by the data processor 230 is also included in the OCT image.

Further, the data processor 230 determines the focus state of the measurement light LS in fine focus adjustment control by analyzing the detection result of the interference light obtained by the OCT measurement. For example, the main controller 211 performs repetitive OCT measurements while controlling the focusing driver 43A according to a predetermined algorithm. The data processor 230 analyzes detection results of interference light LC repeatedly acquired by the OCT measurements to calculate predetermined evaluation values relating to image quality of OCT images. The data processor 230 determines whether the calculated evaluation value is equal to or less than a threshold. In some embodiments, the fine focus adjustment is continued until the calculated evaluation value becomes equal to or less than the threshold. That is, when the evaluation value is equal to or less than the threshold, it is determined that the focus state of the measurement light LS is appropriate. And the fine focus adjustment is continued until it is determined that the focus state of the measurement light LS is appropriate.

In some embodiments, the main controller 211 monitors the intensity of the interference signal (interference intensity, interference sensitivity) acquired sequentially while acquiring the interference signal by performing the repetitive OCT measurements as described above. In addition, while performing this monitoring process, the OCT focusing lens 43 is moved to find the position of the OCT focusing lens 43 in which the interference intensity is maximized. With the fine focus adjustment thus performed, the OCT focusing lens 43 can be guided to the position where the interference intensity is optimized.

Further, the data processor 230 determines the polarization state of at least one of the measurement light LS and the reference light LR by analyzing the detection result of the interference light obtained by the OCT measurement. For example, the main controller 211 performs repetitive OCT measurements while controlling at least one of the polarization controllers 103 and 118 according to a predetermined algorithm. In some embodiments, the main controller 211 controls the attenuator 120 to change an attenuation of the reference light LR. The data processor 230 analyzes detection results of interference light LC repeatedly acquired by the OCT measurements to calculate predetermined evaluation values relating to image quality of OCT images. The data processor 230 determines whether the calculated evaluation value is equal to or less than a threshold. The threshold is set in advance. Polarization adjustment is continued until the evaluation value calculated becomes equal to or less than the threshold. That is, when the evaluation value is equal to or less than the threshold, it is determined that the polarization state of the measurement light LS is appropriate. And the polarization adjustment is continued until it is determined that the polarization state of the measurement light LS is appropriate.

In some embodiments, the main controller 211 can monitor the interference intensity also in the polarization adjustment.

Further, the data processor 230 performs predetermined analysis processing on the detection result of the interference light acquired by performing OCT measurement or the OCT image formed based on the detection result. Examples of the predetermined analysis processing include specifying (identification) of a predetermined site (tissue, lesion) of the subject's eye E; calculation of a distance, area, angle, ratio, or density between designated sites (distance between layers, interlayer distance); calculation by a designated formula; specifying of the shape of a predetermined site; calculation of these statistics; calculation of distribution of the measured value or the statistics; image processing based on these analysis processing results, and the like. Examples of the predetermined tissue include a blood vessel, an optic disc, a fovea, a macula, and the like. Examples of the predetermined lesion include a leukoma, a hemorrhage, and the like.

The data processor 230 performs coordinate transformation on the pixel positions in the OCT image so that the site in the eye in the acquired OCT image is drawn in actual shape.

That is, the data processor 230 corrects the OCT image (or two-dimensional or three-dimensional scan data) of the subject's eye obtained by scanning inside the eye with the measurement light using the optical scanner arranged at a position substantially optically conjugate to the predetermined site in the subject's eye E. Examples of the predetermined site include a pupil. For example, the OCT image is formed by arranging a plurality of A-scan images acquired by scanning inside the subject's eye with the measurement light deflected around the predetermined site of the subject's eye. A-scan center position of the scanning is arranged at the predetermined site. For example, the two-dimensional or three-dimensional scan data is formed by arranging a plurality of A-scan data acquired by scanning inside the subject's eye with the measurement light deflected around the predetermined site of the subject's eye. The scan center position of the scanning is arranged at the predetermined site.

The data processor 230 specifies a transformed position along an A-scan direction (traveling direction of the measurement light passing through the predetermined site of the subject's eye). Here, the transformed position corresponds to a pixel position in the OCT image (or a scan position in the two-dimensional or three-dimensional scan data). The data processor 230 transforms the pixel position (or scan position) into the transformed position specified based on the pixel position or the like. The transformed position is a position in a predetermined coordinate system. The predetermined coordinate system is defined by two or more coordinate axes including an coordinate axis in the same axial direction as the scan direction of at least one A-scan.

In some embodiments, the data processor 230 specifies the transformed position based on a parameter representing optical characteristics of the subject's eye E. In some embodiments, the data processor 230 specifies at least one of a component of a first axis direction of the transformed position and a component of a second axis direction of the transformed position, the second axis direction intersecting the first axis direction, in a predetermined coordinate system, based on a scan radius in the A-scan direction, a scan angle, a depth range that can be measured using OCT and the pixel position (or scan position).

This allows to correct the shape of the site in the eye such as the fundus represented in the OCT image (or scan data) to the shape along the direction of the actual scan. In particular, the actual shape can be easily grasped from the OCT image (or scan data), which is acquired using a w % ide-angle imaging system or an observation system. Further, morphology information representing the morphology of the subject's eye can also be acquired as the information representing the actual morphology, using the corrected OCT image (or two-dimensional or three-dimensional scan data).

Further, the data processor 230 can correct the pixel value at the first position in the predetermined site in the eye in the OCT image before or after the coordinate transformation described above, based on the pixel value in the corresponding front image of the subject's eye E to generate the correction OCT image, in order to apply the grayscale representing of the front image to the OCT image. Further, the data processor 230 can obtain a distance between predetermined sites in the eye using the OCT image (or correction OCT image) after coordinate transformation.

Such data processor 230 includes a shape correcting unit 231, a layer region specifying unit 232, a pixel position specifying unit 233, an image correcting unit 234, and an intraocular distance calculator 235, as shown in FIG. 4.

Shape Correcting Unit

The shape correcting unit 231 performs coordinate transformation on the pixel positions in the OCT image so that the site in the eye in the OCT image is drawn in actual shape.

Figure 6:
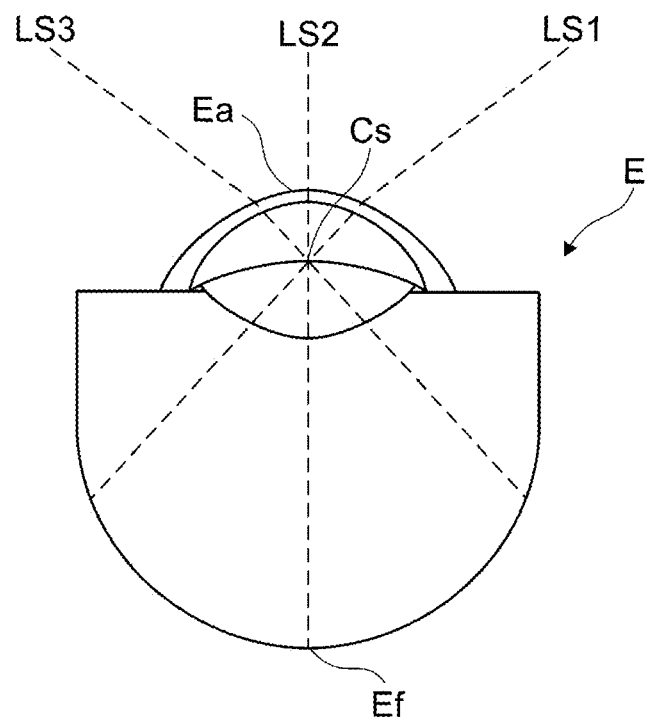
FIG. 6 is a schematic diagram for explaining processing performed by an ophthalmological apparatus according to a comparative example of the embodiments.

FIG. 6 shows a diagram of comparative examples of the embodiments. FIG. 6 schematically shows the path of the measurement light incident on the subject's eye E.

The measurement light deflected by the optical scanner 42, for example, is incident on the pupil of the subject's eye E, which is a scan center position, at various incident angles, as shown in FIG. 6. The measurement light incident on the subject's eye E is projected toward each part in the eye around the scan center position Cs set at the center of the pupil, for example.

An A-scan image is formed from the interference data obtained using the measurement light LS1 in FIG. 6, an A-scan image is formed from the interference data obtained using the measurement light LS2, and an A-scan image is formed from the interference data obtained using the measurement light LS3. The tomographic image is formed by arranging the plurality of A-scan images formed like this in the horizontal direction.

In this way, the A-scan directions vary within the scan angle range centered on the scan center position Cs, and the shape of the site is deformed in the tomographic images in which the obtained plurality of A-scan images are arranged in the horizontal direction. The wider the angle of view is, the greater the difference from the actual shape becomes.

Further, morphology information representing the morphology of the subject's eye E can be obtained from the positions of arbitrary pixels in the tomographic image. Examples of the morphology information include an intraocular distance (including a distance between layer regions), an area of region, a volume of region, a perimeter of region, a direction of site with reference to a reference position, an angle of site with reference to a reference direction, and a curvature radius of site.

For example, the intraocular distance as the morphology information can be obtained by measuring a distance between arbitrary two points in the tomographic image. In this case, the distance between the two points can be specified using the number of pixels in the tomographic image, and can be measured by multiplying the specified number of pixels by the pixel size specific to the apparatus. At this time, the same pixel size is adopted for all pixels in the tomographic image. However, as described above, the scan directions are different with the scan center position Cs as the center. Thereby, the pixel size in the horizontal direction of the tomographic image differs depending on the depth position in the scan direction. For example, in case that the depth range is 2.5 millimeters, when the same pixel size is adopted for all pixels in the tomographic image, there is a difference of about 13% in the scan length of the B-scan between the upper portion and the lower portion of the tomographic image, and when the depth range is 10 millimeters, there is a difference of about 50%.

In contrast, the data processor 230 according to the embodiments performs coordinate transformation on the pixel positions in the acquired OCT image (or scan positions in the scan data). Hereinafter, the intraocular distance will be described as an example of the morphology information representing the morphology of the subject's eye E.

As shown in FIG. 5, the shape correcting unit 231 includes a transformed position specifying unit 231A, a transforming unit 231B, and an interpolating unit 231C.

Transformed Position Specifying Unit

The transformed position specifying unit 231A is configured to specify a transformed position along the traveling direction of the measurement light passing through the scan center position Cs, the transformed position corresponding to the pixel position in the OCT image (or the scan position in the scan data). In some embodiments, the transformed position specifying unit 231A uses the eyeball parameter 212A for performing processing for specifying the transformed position.

Figure 7:
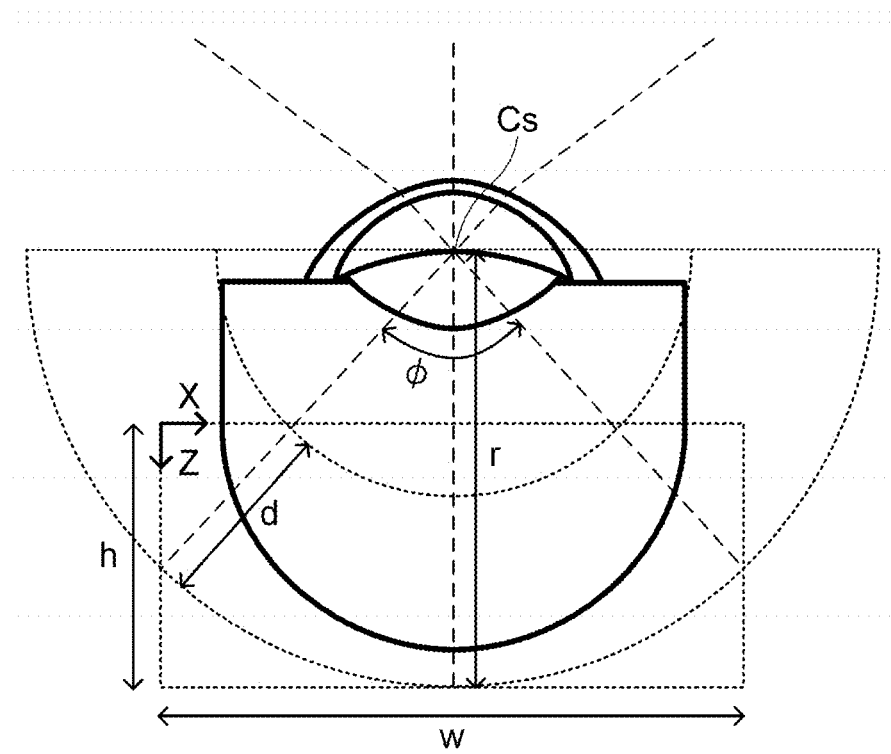
FIG. 7 is a schematic diagram for explaining processing performed by the ophthalmological apparatus according to the embodiments.

FIG. 7 shows a diagram describing the operation of the transformed position specifying unit 231A according to the embodiments. FIG. 7 shows a diagram describing the operation of the transformed position specifying unit 231A in the two-dimensional OCT image. In FIG. 7, parts similarly configured to those in FIG. 6 are denoted by the same reference numerals, and the description thereof is omitted unless it is necessary.

Here, the scan angle is "$\varphi$", the scan radius is "r", the depth range in which OCT measurement can be performed is "d", the length of the tomographic image in the depth direction is "h", and the lateral length of the tomographic image is "w". The scan angle $\varphi$ corresponds to the deflection angle of the measurement light LS around the scan center position Cs. The scan radius r corresponds to the distance from the scan center position Cs to a zero optical path length position where the measurement optical path length and the reference optical path length are substantially equal. The depth range d is a value (known) specific to the apparatus, the value being uniquely determined by the optical design of the apparatus.

The transformed position specifying unit 231A specifies the transformed position (X, Z) in a second coordinate system from the pixel position (x, z) in a first coordinate system. The first coordinate system is a coordinate system having the origin at the upper left coordinate position in the OCT image (B-scan image). The first coordinate system is defined by an x coordinate axis having the B-scan direction as the x direction and a z coordinate axis, which is orthogonal to the x coordinate axis, having the A-scan direction as the z direction. The pixel position (x, z) in the OCT image is defined in the first coordinate system. The second coordinate system is defined a Z coordinate axis (for example, second axis) and a X coordinate axis (for example, first axis). The Z coordinate axis has the traveling direction of the measurement light LS having the scan angle of 0 degrees with respect to the measurement optical axis passing through a predetermined site (for example, fovea) in the fundus Ef, as the Z direction. The X coordinate axis has the B-scan direction orthogonal to the Z coordinate axis at the predetermined site, as the X direction. In the second coordinate system, a predetermined Z position is set as the origin of the Z coordinate axis so that the position of the scan radius r becomes the deepest portion in the measurement optical axis passing through the predetermined site (for example, the fovea). Further, a predetermined X position in the measurement optical axis passing through the predetermined site (for example, the fovea) is set as the origin of the X coordinate axis so as to have a predetermined depth direction length d as described below. The transformed position (X, Z) is defined in the second coordinate system. The transformed position (X, Z) corresponds to the pixel position (x, z), and is a position along the traveling direction of the measurement light LS passing through the scan center position Cs (A-scan direction).

The transformed position specifying unit 231A specifies the transformed position (X, Z) based on the scan radius r of the A-scan direction, the scan angle $\varphi$, the depth range d in which the OCT measurement can be performed, and the pixel position (x, z). The transformed position specifying unit 231A can specify at least one of the X component of the transformed position (component of the first axis direction) and the Z component of the transformed position (component of the second axis direction).

For the OCT image (tomographic image) in which the number of A-scan lines is "N" (N is a natural number), the transformed position (X, Z), which corresponds to the pixel position (x, z) in the n-th (n is a natural number) A-scan line, is specified as shown in Equations (1) and (2).

[Equation 1]

$$X = \frac{w}{2} + (r - d + z) \times \sin\left(\frac{\varphi}{N} \times n - \frac{\varphi}{2}\right) \quad (1)$$

[Equation 2]

$$Z = (r - d + z) \times \cos\left(\frac{\varphi}{N} \times n - \frac{\varphi}{2}\right) - (r - d) \times \cos\frac{\varphi}{2} \quad (2)$$

Here, the length "h" in the depth direction of the OCT image, the length "w" in the horizontal direction of the OCT image, and the x component of the pixel position are expressed by Equations (3) to (5).

[Equation 3]

$$h = r - (r - d) \times \cos\frac{\varphi}{2} \quad (3)$$

[Equation 4]

$$w = 2r \times \sin\frac{\varphi}{2} \quad (4)$$

[Equation 5]

$$x = n \quad (5)$$

In Equations (1) and (2), the x coordinate of the pixel position is expressed by Equation (5). Thus, the transformed position specifying unit 231A can specify the transformed position (X, Z) from the pixel position (x, z), based on the scan radius r, the scan angle $\varphi$, and the depth range d.

In some embodiments, for the scan data, the transformed position specifying unit 231A can specify the transformed position (X, Z) based on the scan radius r in the A-scan direction, the scan angle $\varphi$, the depth range d in which the OCT measurement can be performed, and the scan position, in the same way as above.

In some embodiments, the scan radius r is specified by analyzing the detection result of the interference light LC obtained using the OCT optical system 8. This allows to specify the transformed position (X, Z) that more accurately reflects the eyeball optical characteristics of subject's eye E.

In some embodiments, the transformed position specifying unit 231A specifies the scan angle $\varphi$ by performing ray trace processing on the measurement light LS based on the corneal shape information of the subject's eye E. Examples of the corneal shape information include a corneal curvature radius (curvature radius of an anterior surface of cornea, curvature radius of a posterior surface of cornea) and corneal thickness. This allows to specify the transformed position (X, Z) that more accurately reflects the eyeball optical characteristics of subject's eye E.

Figure 8:
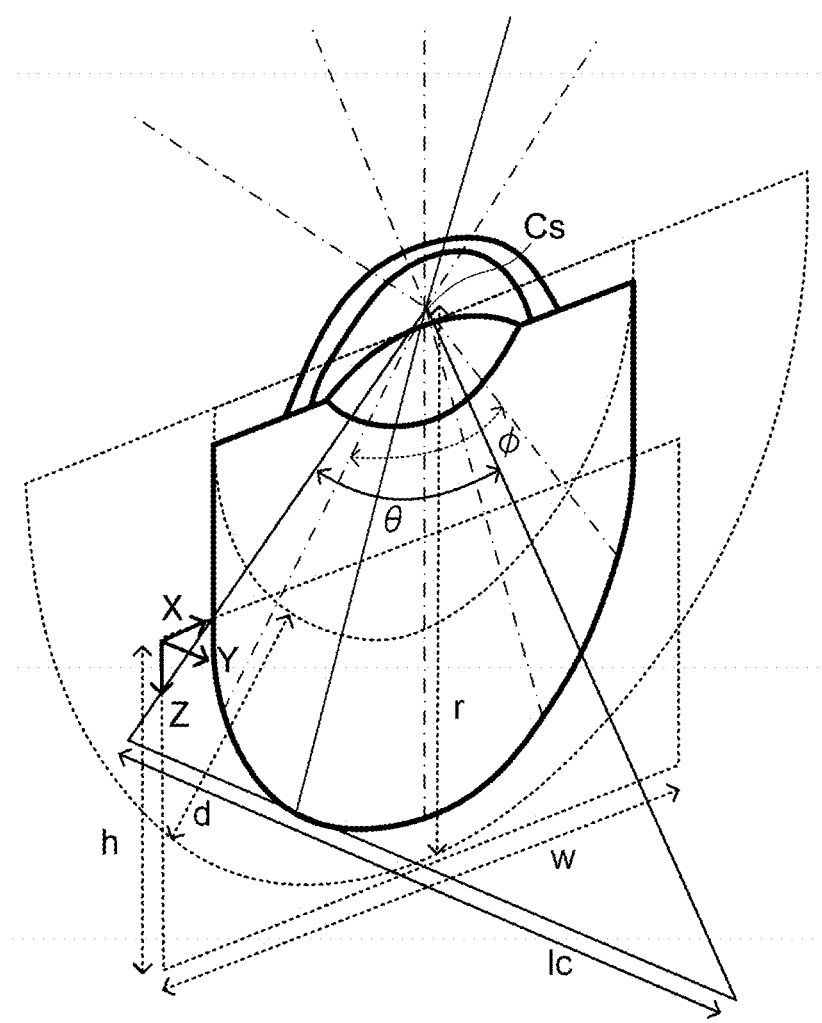
FIG. 8 is a schematic diagram for explaining processing performed by the ophthalmological apparatus according to the embodiments.

FIG. 8 shows a diagram describing the operation of the transformed position specifying unit 231A according to the embodiments. FIG. 8 shows a diagram describing the operation of the transformed position specifying unit 231A in the three-dimensional OCT image. In FIG. 8, parts similar to those in FIG. 7 are denoted by the same reference symbols, and description thereof is omitted as appropriate.

In FIG. 8, a Y plane is defined in addition to the X plane and the Z plane in FIG. 7. In addition to the parameters shown in FIG. 7, the central angle in the C-scan direction is "θ", and the length in the C-scan direction is "lc".

The transformed position specifying unit 231A specifies the transformed position (X Y, Z) in a fourth coordinate system from the pixel position (x y, z) in a third coordinate system. The third coordinate system is a coordinate system having the origin at the upper left coordinate position in the three-dimensional OCT image. The third coordinate system is defined by the x coordinate axis having the B-scan direction as the x direction, a y coordinate axis, which is orthogonal to the x coordinate axis, having the C-scan direction as the y direction, and the z coordinate axis, which is orthogonal to both of the x coordinate axis and the y coordinate axis, having the A-scan direction as the z direction. The pixel position (x, y, z) in the OCT image is defined in the third coordinate system. The fourth coordinate system is defined the Z coordinate axis, the X coordinate axis, and a Y coordinate axis. The Z coordinate axis has the traveling direction of the measurement light LS having the scan angle of 0 degrees with respect to the measurement optical axis passing through a predetermined site (for example, fovea) in the fundus Ef, as the Z direction. The X coordinate axis has the B-scan direction orthogonal to the Z coordinate axis at the predetermined site, as the X direction. The Y coordinate axis has the C-scan direction orthogonal to the Z coordinate axis at the predetermined site, as the Y direction. In the fourth coordinate system, a predetermined Z position is set as the origin of the Z coordinate axis so that the position of the scan radius r becomes the deepest portion in the measurement optical axis passing through the predetermined site (for example, the fovea). Further, a predetermined X position and Y position in the measurement optical axis passing through the predetermined site (for example, the fovea) are set as the origin of the X coordinate axis and the Y coordinate axis so as to have a predetermined depth direction length d as described below. The transformed position (X, Y. Z) is defined in the fourth coordinate system. The transformed position (X, Y. Z) corresponds to the pixel position (x, y, z), and is a position along the traveling direction of the measurement light LS passing through the scan center position Cs (A-scan direction).

The transformed position specifying unit 231A can specify at least one of the X component, the Y component, and the Z component of the transformed position.

For the OCT image (tomographic image) in which the number of A-scan lines is "N" (N is a natural number) and the number of B-scan lines is "M" (M is a natural number), the transformed position (X, Y, Z), which corresponds to the pixel position (x, y, z) in the n-th (n is a natural number) A-scan line of the m-th (m is a natural number) B-scan line, is specified as shown in Equations (6) to (8).

[Equation 6]
$$X = \frac{w}{2} + \frac{(r-d+z) \times \tan\left(\frac{\varphi}{N} \times n - \frac{\varphi}{2}\right)}{\sqrt{\tan^2\left(\frac{\varphi}{N} \times n - \frac{\varphi}{2}\right) + \tan^2\left(\frac{\theta}{M} \times m - \frac{\theta}{2}\right) + 1}} \quad (6)$$

[Equation 7]
$$Y = \frac{lc}{2} + \frac{(r-d+z) \times \tan\left(\frac{\theta}{N} \times m - \frac{\theta}{2}\right)}{\sqrt{\tan^2\left(\frac{\varphi}{N} \times n - \frac{\varphi}{2}\right) + \tan^2\left(\frac{\theta}{M} \times m - \frac{\theta}{2}\right) + 1}} \quad (7)$$

[Equation 8]
$$Z = \frac{(r-d+z)}{\sqrt{\tan^2\left(\frac{\varphi}{N} \times n - \frac{\varphi}{2}\right) + \tan^2\left(\frac{\theta}{M} \times m - \frac{\theta}{2}\right) + 1}} - (r-h) \quad (8)$$

Here, the x component and the y component of the pixel position are expressed by Equations (9) to (13) from the length h in the depth direction, the length w in the B-scan direction, and the length lc in the C-scan direction of the three-dimensional OCT image.

[Equation 9]
$$h = r - (r-d) \times \cos\frac{\varphi}{2} \quad (9)$$

[Equation 10]
$$w = 2r \times \sin\frac{\varphi}{2} \quad (10)$$

[Equation 11]
$$lc = 2r \times \sin\frac{\theta}{2} \quad (11)$$

[Equation 12]
$$x = n \quad (12)$$

[Equation 13]
$$y = m \quad (13)$$

In Equations (6) to (8), the x coordinate and the y coordinate of the pixel position are expressed by Equations (12) and Equation (13). Thus, the transformed position specifying unit 231A can specify the transformed position (X, Y, Z) from the pixel position (x, y, z), based on the scan radius r, the scan angle φ, and the depth range d.

In some embodiments, for the scan data, the transformed position specifying unit 231A can specify the transformed position (X, Y, Z), in the same way as above.

Transforming Unit

In case that the OCT image is a two-dimensional image, the transforming unit 231B transforms the pixel position (x, z) in the OCT image shown in FIG. 7 into the transformed position (X, Z) specified by the transformed position specifying unit 231A. In some embodiments, for each of all pixel positions in the OCT image, the transformed position specifying unit 231A specifies the transformed position and the transforming unit 231B transforms the pixel position into the transformed position.

Figure 9:
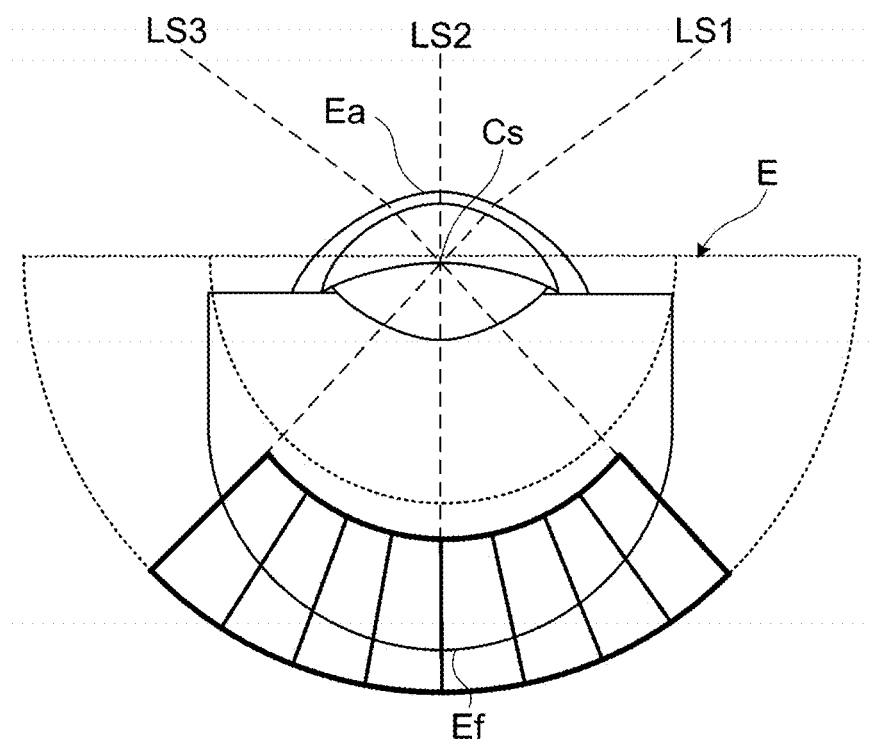
FIG. 9 is a schematic diagram for explaining processing performed by the ophthalmological apparatus according to the embodiments.

This allows to arrange the A-scan images, which are acquired by performing A-scan, in the A-scan direction as shown in FIG. 9. Therefore, even if the angle of view is wide, the tomographic image in which the shape of the predetermined site is similar to the actual shape can be obtained.

Further, in case that the OCT is a three-dimensional image, the transforming unit 231B can transform the pixel position (x, y, z) in the OCT image shown in FIG. 8 into the transformed position (X, Y, Z) specified by the transformed position specifying unit 231A. In some embodiments, for each of all pixel positions in the OCT image, the transformed position specifying unit 231A specifies the transformed position and the transforming unit 231B transforms the pixel position into the transformed position.

Interpolating Unit

The interpolating unit 231C interpolates pixels between the transformed positions. For example, intervals between the A-scan images adjacent to each other in which the pixel positions have been transformed into the transformed position varies depending on the distance from the scan center position Cs. The interpolating unit 231C interpolates pixel (s) between the A-scan images using a pixel in the A-scan images adjacent to each other according to the depth position in the A-scan image. As interpolation processing on pixels performed by the interpolating unit 231C, a known method such as a nearest neighbor method, a bilinear interpolation method, or a bicubic interpolation method can be adopted. In some embodiments, the interpolating unit 231C interpolates pixels between the A-scan images adjacent to each other according to the distance from the scan center position Cs. For example, the interpolating unit 231C interpolates pixels between the A-scan images adjacent to each other by changing interpolation processing method according to the distance from the scan center position Cs.

In some embodiments, for the scan position in the scan data, the scan data is interpolated, in the same way as above.

Layer Region Specifying Unit

The layer region specifying unit 232 shown in FIG. 4 specifies an image region corresponding to a predetermined layer region of the fundus Ef by analyzing the tomographic image corrected by the shape correcting unit 231 (or the OCT image before correcting). Examples of the layer region of the fundus Ef include the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer, the choroid, the sclera, and the boundary surfaces of each layer region.

Processing for specifying the predetermined layer region from the OCT image includes the segmentation processing. The segmentation processing is known processing for specifying a partial region in an OCT image. The layer region specifying unit 232 performs, for example, segmentation processing based on a brightness value of each pixel in the OCT image. That is, each of the layer regions of the fundus Ef has a characteristic reflectance, and image regions corresponding to these layer regions also have characteristic brightness values. The layer region specifying unit 232 can specify a target image region (layer region) by performing segmentation processing based on these characteristic brightness values.

In the present embodiment, a pixel value in the image region corresponding to any of the above layer regions specified by the layer region specifying unit 232 is corrected based on a pixel value at a corresponding position in the front image. Examples of the layer region where the pixel value is corrected in this way include a layer region specified as the most superficial layer of the fundus Ef, and a layer region where the intensity of the interference signal is high (or highest).

Pixel Position Specifying Unit

The pixel position specifying unit 233 specifies the second position in the front image (fundus image) of the fundus Ef corresponding to the first position in the layer region (predetermined site) specified by the layer region specifying unit 232. In some embodiments, the first position means the positions of all pixels in the image region corresponding to the layer region specified by the layer region specifying unit 232. In some embodiments, the first position is a representative position in the image region corresponding to the layer region specified by the layer region specifying unit 232. In some embodiments, the first position is a position designated using the operation unit 240B described below for the image region corresponding to the layer region specified by the layer region specifying unit 232.

For example, the pixel position specifying unit 233 specifies the pixel position in the front image corresponding to the pixel position in the OCT image, using a reference position in the front image, a reference position in the OCT image, a position of a characteristic site of the subject's eye E depicted in the front image, and a position of the characteristic site depicted in the OCT image. Examples of the reference position in the front image include a position of the optical axis of the imaging optical system 30 in the front image. Examples of the reference position in the OCT image include a position of the optical axis of the interference optical system (optical system included in the OCT unit 100) in the OCT image. Examples of the characteristic site include an optic disc, a fovea, a blood vessel, a lesion, and a scar after treatment. In some embodiments, considering the magnification of the optical system, the pixel position in the front image corresponding to the pixel position in the OCT image is specified.

In some embodiments, the front image is acquired using the imaging optical system 30 under predetermined imaging conditions, and the OCT image is acquired using the OCT unit 100 under predetermined measurement conditions. In this case, the pixel position specifying unit 233 specifies the second position in the front image of the subject's eye E, the second position corresponding to the first position, by transforming the first position of the fundus in the OCT image, according to the transformation equation corresponding to the imaging conditions and the measurement conditions (for example, a predetermined transformation equation).

Image Correcting Unit

The image correcting unit 234 corrects a pixel value in a region including the first position in the predetermined site in the OCT image corrected by the shape correcting unit 231 (or OCT image before correcting) based on a pixel value at the second position corresponding to the first position specified by the pixel position specifying unit 233 (second position corresponding to the first position in the front image). The region including the first position may be an image region corresponding to the first position or an image region of a predetermined size that includes the pixel corresponding to the first position.

In some embodiments, the image correcting unit 234 sets the pixel value at the second position as the pixel value in the region including the above first position. In some embodiments, the image correcting unit 234 sets the pixel value corresponding to the pixel value at the second position as the pixel value in the region including the above first position. The pixel value corresponding to the pixel value at the second position is determined according to the relationship (difference, ratio, etc.) between the overall luminance distribution of the front image and the overall luminance distribution of the OCT image.

In some embodiments, in case that a plurality of pixels is included in the region including the first position, the pixel value of each pixel is corrected based on the pixel value at the second position according to the original pixel value.

In some embodiments, in case that a plurality of pixels is included in the region including the first position, the pixel value of each pixel is corrected based on the pixel value at the second position regardless of the original pixel value. For example, the pixel value of each pixel is set to the pixel value at the second position, or the pixel value corresponding to the pixel value at the second position.

Figure 10:
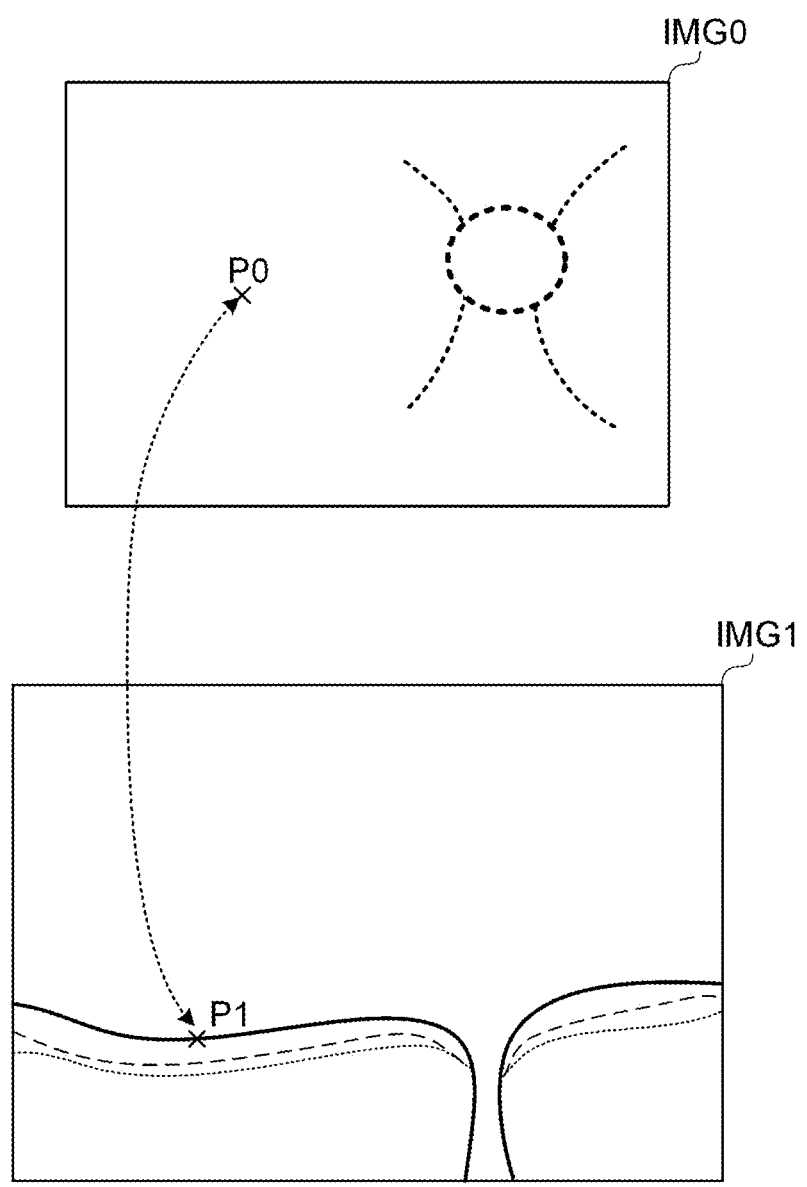
FIG. 10 is a schematic diagram for explaining processing performed by the ophthalmological apparatus according to the embodiments.

FIG. 10 shows a diagram describing the operation of the pixel position specifying unit 233 and the image correcting unit 234 according to the embodiments. FIG. 10 schematically represents the color front image IMG) of the fundus Ef of the subject's eye E and the tomographic image IMG1 (two-dimensional OCT image) of the fundus Ef of the subject's eye E. In FIG. 10, the tomographic image IMG1 is the OCT image corrected by the shape correcting unit 231 or the OCT image before correcting.

As shown in FIG. 10, the pixel position specifying unit 233 specifies the second position P0 in the front image IMG0 of the subject's eye E corresponding to the first position P1 in the fundus Ef in the tomographic image IMG1. The image correcting unit 234 corrects the pixel value in the region including the first position P1 in the tomographic image IMG1, based on the pixel value at the second position P0 in the front image IMG0, as described above.

The controller 210 (main controller 211), as the display controller, can display the OCT image corrected by the image correcting unit 234 on the display unit 240A.

In FIG. 10, the case where the OCT image is a two-dimensional image has been described. However, the same applies to the case where the OCT image is a three-dimensional image.

Intraocular Distance Calculator

The intraocular distance calculator 235 shown in FIG. 4 calculates an intraocular distance of the subject's eye E based on the OCT image in which the pixel position has been transformed into the transformed position by shape correcting unit 231.

The intraocular distance calculator 235 obtains the intraocular distance between predetermined sites in the subject's eye E based on the OCT image transformed by the transforming unit 231B or the OCT image corrected by the image correcting unit 234, for example. For example, the intraocular distance calculator 235 specifies predetermined sites inside the eye by analyzing the OCT image, and obtains the above intraocular distance based a distance between the specified sites. The distance between the two points can be specified using the number of pixels in the image, and can be measured by multiplying the specified number of pixels by the pixel size specific to the apparatus. In this case, the same pixel size is adopted for all pixels in the image.

Examples of the intraocular distance between the predetermined sites include a distance between designated sites (tissues, layer regions), an axial length, and a distance from a scan center position of the measurement light, which is set at the center of the pupil, or the like, to a retina. In case that the axial length is obtained as the intraocular distance, the intraocular distance calculator 235 obtains the axial length based on a distance from a site corresponding to a corneal apex to a site corresponding to the retina.

The data processor 230 that functions as above includes, for example, a processor described above, a RAM, a ROM, a hard disk drive, a circuit board, and the like. In a storage device such as the hard disk drive, a computer program for causing the processor to execute the functions described above is stored in advance.

User Interface

The user interface 240 includes the display unit 240A and the operation unit 240B. The display unit 240A includes the aforementioned display device of the arithmetic control unit 200 and/or the display apparatus 3. The operation unit 240B includes the aforementioned operation device of the arithmetic control unit 200. The operation unit 240B may include various kinds of buttons and keys provided on the housing of the ophthalmological apparatus 1, or provided outside the ophthalmological apparatus 1. For example, when the fundus camera unit 2 has a case similar to that of the conventional fundus camera, the operation unit 240B may include a joy stick, an operation panel, and the like provided to the case. Further, the display unit 240A may include various kinds of display devices, such as a touch panel placed on the housing of the fundus camera unit 2.

It should be noted that the display unit 240A and the operation unit 240B need not necessarily be formed as separate devices. For example, a device like a touch panel, which has a display function integrated with an operation function, can be used. In such cases, the operation unit 240B includes the touch panel and a computer program. The content of operation performed on the operation unit 240B is fed to the controller 210 as an electric signal. Moreover, operations and inputs of information may be performed using a graphical user interface (GUI) displayed on the display unit 240A and the operation unit 240B.

The imaging optical system 30, the optical system in the path from the interference optical system included in the OCT unit 100 to the objective lens 22, and the image forming unit 220 (or the optical system in the path from the interference optical system included in the OCT unit 100 to the objective lens 22, the image forming unit 220, and the data processor 230) are an example of the "acquisition unit" according to the embodiments. The pixel position specifying unit 233 is an example of the "position specifying unit" according to the embodiments. The controller 210 (main controller 211) is an example of the "display controller" according to the embodiments. The display apparatus 3 or the display unit 240A is an example of the "display means" according to the embodiments. The imaging optical system 30 is an example of the "imaging unit" according to the embodiments. The optical system in the path from the interference optical system included in the OCT unit 100 to the objective lens 22, and the image forming unit 220 (or the optical system in the path from the interference optical system included in the OCT unit 100 to the objective lens 22, the image forming unit 220, and the data processor 230) an example of the "OCT unit" according to the embodiments.

Operation

The operation of the ophthalmological apparatus 1 according to the embodiments will be described.

Figure 11:
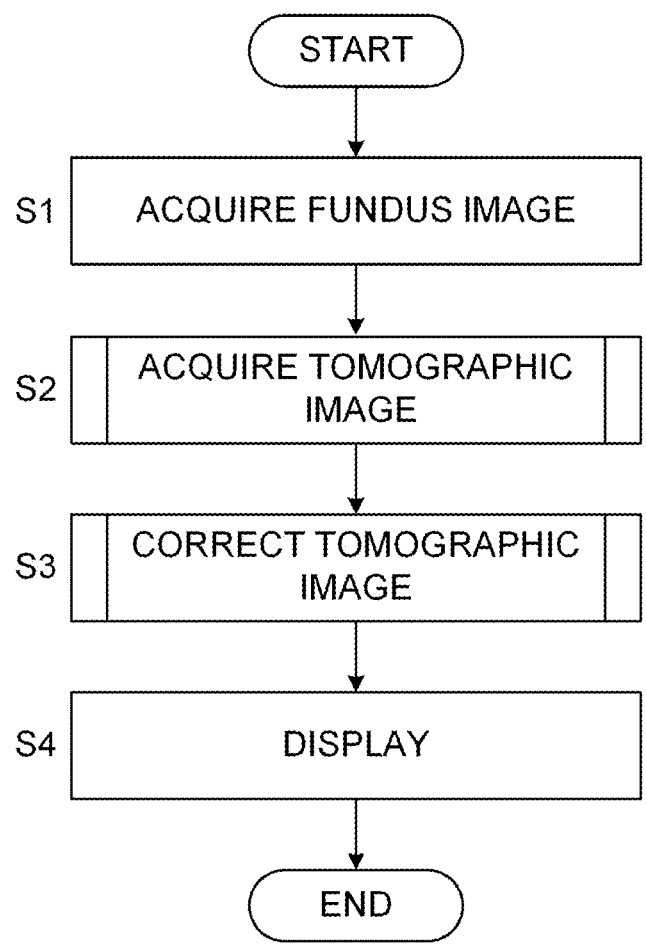
FIG. 11 is a schematic diagram illustrating an example of an operation of the ophthalmological apparatus according to the embodiments.
Figure 12:
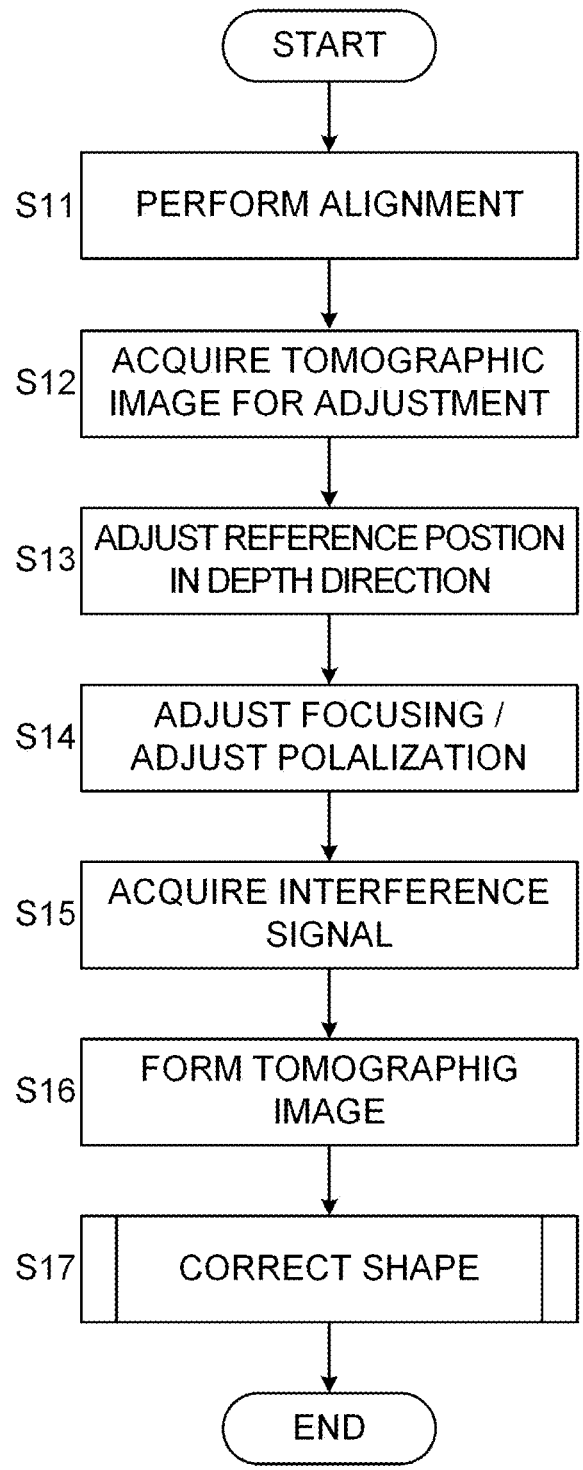
FIG. 12 is a schematic diagram illustrating an example of an operation of the ophthalmological apparatus according to the embodiments.
Figure 13:
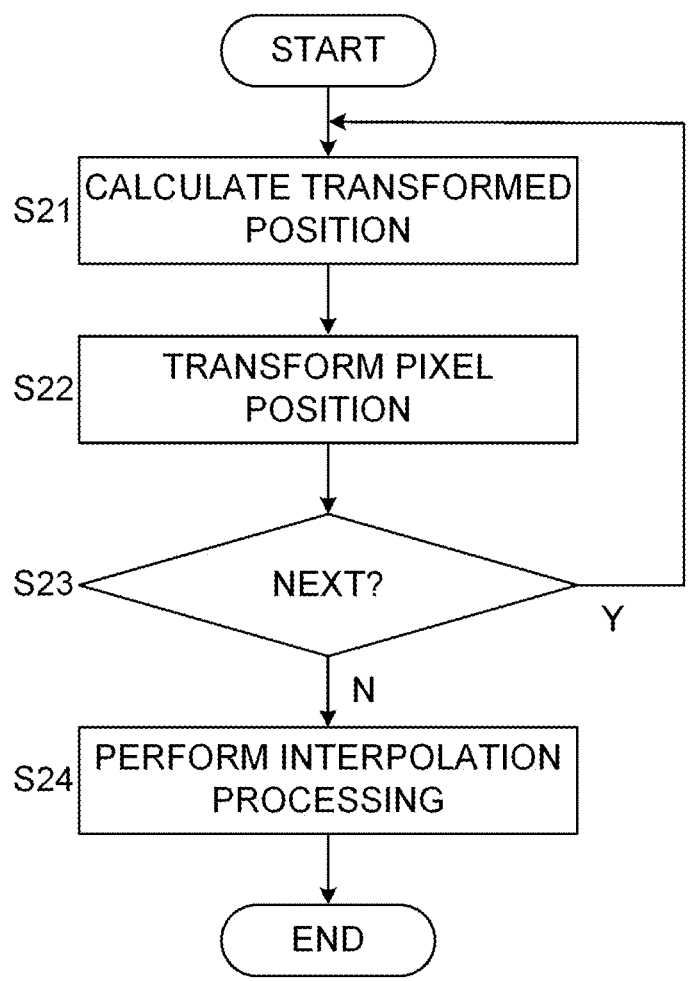
FIG. 13 is a schematic diagram illustrating an example of an operation of the ophthalmological apparatus according to the embodiments.
Figure 14:
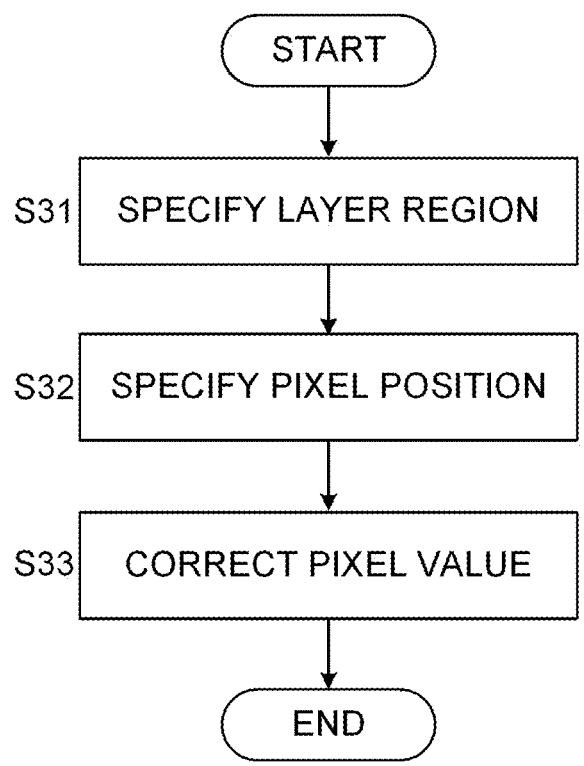
FIG. 14 is a schematic diagram illustrating an example of an operation of the ophthalmological apparatus according to the embodiments.

FIGS. 11 to 14 show examples of the operation of the ophthalmological apparatus 1 according to the embodiments. FIGS. 11 to 14 show flowcharts of the examples of the operation of the ophthalmological apparatus 1 according to the embodiments. FIG. 12 shows a flowchart of an example of the operation of step S2 in FIG. 11. FIG. 13 shows a flowchart of an example of the operation of step S17 in FIG. 12. FIG. 14 shows a flowchart of an example of the operation of step S3 in FIG. 11. The storage unit 212 stores computer programs for realizing the processing shown in FIGS. 11 to 14. The main controller 211 operates according to the computer programs, and thereby the main controller 211 performs the processing shown in FIGS. 11 to 14.

S1: Acquire Fundus Image

First, the main controller 211 performs alignment.

That is, the main controller 211 controls the alignment optical system 50 to project the alignment indicator onto the subject's eye E. At this time, a fixation target generated by the LCD 39 is also projected onto the subject's eye E. The main controller 211 controls the movement mechanism 150 based on the movement amount of the optical system to relatively to move the optical system with respect to the subject's eye E by the movement amount. The movement amount is specified based on the receiving light image obtained using the image sensor 35, for example. The main controller 211 repeatedly performs this processing.

And then, the main controller 211 controls the imaging optical system 30 to obtain the fundus image as the front image of the fundus Ef of the subject's eye E, using the image sensor 38 (or image sensor 35). In this case, the main controller 211 controls the LCD 39 to display the fixation target for OCT measurement at a predetermined position on the LCD 39. The main controller 211 can display the fixation target at a display position on the LCD 39 corresponding to a position of an optical axis of the optical axis on the fundus Ef.

S2: Acquire Tomographic Image

Subsequently, the main controller 211 controls the OCT unit 100 and the like to acquire tomographic image of the fundus Ef of the subject's eye E. The details of step S2 will be described below.

S3: Correct Tomographic Image

Next, the main controller 211 controls the layer region specifying unit 232, the pixel position specifying unit 233, and the image correcting unit 234 to correct the tomographic image acquired in step S2, using the fundus image acquired in step S1. The details of step S3 will be described below.

S4: Display

The main controller 211 controls the display unit 240A to display the tomographic image corrected in step S3. In some embodiments, the main controller 211 displays the fundus image acquired in step S1 and the tomographic image corrected in step S3 on the same screen of the display unit 240A. In some embodiments, the main controller 211 displays the first position and the second position identifiably so as to be capable of grasping the correspondence between the first position in the tomographic image specified in step S3 and the second position in the fundus image.

This terminates the operation of the ophthalmological apparatus 1 (END).

In step S2 in FIG. 11, processing is performed according to the flow shown in FIG. 12.

S11: Perform Alignment

The main controller 211 performs alignment, in the same manner as in step S1.

In some embodiments, the processing in step S11 is omitted. In some embodiments, the rough alignment adjustment and the fine alignment adjustment are performed after the alignment in step S11 is completed.

S12: Acquire Tomographic Image for Adjustment

The main controller 211 controls the LCD 39 to display the fixation target for OCT measurement at a predetermined position on the LCD 39. The main controller 211 can display the fixation target at a display position on the LCD 39 corresponding to a position of an optical axis of the optical axis on the fundus Ef.

Subsequently, the main controller 211 controls the OCT unit 100 to perform OCT provisional measurement, and to acquire a tomographic image for adjusting a reference position of the measurement range in the depth direction. Specifically, the main controller 211 controls the optical scanner 42 to deflect the measurement light LS generated based on the light L0 emitted from the light source unit 101 and to scan fundus Ef of the subject's eye E with the deflected measurement light LS. The detection result of the interference light obtained by scanning with the measurement light LS is sent to the image forming unit 220 after being sampled in synchronization with the clock KC. The image forming unit 220 forms the tomographic image (OCT image) of the subject's eye E from the obtained interference signal.

S13: Adjust Reference Position in Depth Direction

Subsequently, the main controller 211 adjusts the reference position of the measurement range in the depth direction (z direction).

For example, the main controller 211 controls the data processor 230 to specify a predetermined site (for example, sclera) in the tomographic image obtained in step S12, and sets a position separated by a predetermined distance in the depth direction from the specified position of the predetermined site as the reference position of the measurement range. The main controller 211 controls at least one of the optical path length changing units 41 and 114 according to the reference position. Alternatively, a predetermined position determined in advance so that the optical path lengths of the measurement light LS and the reference light LR substantially coincide may be set as the reference position of the measurement range.

S14: Adjust Focusing/Adjust Polarization

Next, the main controller 211 performs control of adjusting focusing and of adjusting polarization.

For example, the main controller 211 controls the OCT unit 100 to perform OCT measurement, after controlling the focusing driver 43A to move the OCT focusing lens 43 by a predetermined distance. The main controller 211 controls the data processor 230 to determine the focus state of the measurement light LS based on the detection result of the interference light acquired by the OCT measurement, as described above. When it is determined that the focus state is not appropriate based on the determination result of the data processor 230, the main controller 211 controls the focusing driver 43A again and repeats this until it is determined that the focus state of the measurement light LS is appropriate.

Further, for example, the main controller 211 controls the OCT unit 100 to perform OCT measurement after controlling at least one of the polarization controllers 103 and 118 to change the polarization state of at least one of the light L0 and the measurement light LS by a predetermined amount. And then, the main controller 211 controls the image forming unit 220 to form the OCT image on the basis of the acquired detection result of the interference light. The main controller 211 controls the data processor 230 to determine the image quality of the OCT image acquired by the OCT measurement. When it is determined that the polarization state is not appropriate based on the determination result of the data processor 230, the main controller 211 controls the polarization controllers 103 and 118 again and repeats this until it is determined that the polanzation state of the measurement light LS is appropriate.

S15: Acquire Interference Signal

Subsequently, the main controller 211 controls the OCT unit 100 to perform OCT measurement. The detection result of the interference light acquired by the OCT measurement is sampled by the DAQ 130 and is stored as the interference signal in the storage unit 212 or the like.

S16: Form Tomographic Image

Next, the main controller 211 controls the image forming unit 220 to form the data set group of the A-scan image data of the subject's eye E based on the interference signal acquired in step S15. The image forming unit 220 forms the tomographic image by arranging the formed A-scan images in the B-scan direction.

S17: Correct Shape

Subsequently, the main controller 211 controls the shape correcting unit 231 to correct the shape of the fundus Ef by correcting the tomographic image formed in step S16. The main controller 211 can correct the tomographic image formed in step S16 using the eyeball parameter 212A stored in the storage unit 212. This allows to acquire the tomographic image in which the A-scan images are arranged in the A-scan direction. The details of step S17 will be described below.

This terminates the processing of step S2 in FIG. 11 (END).

In step S17 in FIG. 12, processing is performed according to the flow shown in FIG. 13.

S21: Calculate Transformed Position

In step S17, the main controller 211 controls the transformed position specifying unit 231A to specify the transformed position corresponding to the pixel position in the tomographic image formed in step S16. The transformed position specifying unit 231A specifies the transformed position corresponding to the pixel position in the tomographic image, as described above.

S22: Transform Pixel Position

Subsequently, the main controller 211 controls the transforming unit 231B to transform the pixel position in the tomographic image into the transformed position calculated in step S21.

S23: Next?

The main controller 211 determine whether or not the next pixel position should be transformed.

When it is determined that the next pixel position should be transformed (S23: Y), the operation of the ophthalmological apparatus 1 proceeds to step S21. When it is determined that the next pixel position should not be transformed (S23: N), the operation of the ophthalmological apparatus 1 proceeds to step S24.

Through steps S21 to S23, for each pixel position of the tomographic image, specifying the transformed position and transforming to the specified transformed position are performed.

S24: Perform Interpolation Processing

When it is determined that the next pixel position should not be transformed in step S23 (S23: N), the main controller 211 controls the interpolating unit 231C to interpolate the pixels between the A-scan images adjacent to each other. A-scan images having been transformed into the transformed positions in step S22.

This terminates the processing of step S17 in FIG. 12 (END).

In step S3 in FIG. 11, processing is performed according to the flow shown in FIG. 14.

S31: Specify Layer Region

In step S3, the main controller 211 controls the layer region specifying unit 232 to specify the predetermined layer region in the tomographic image acquire in step S2. In the present embodiment, the layer region to which the grayscale representation of the fundus image is applied is specified.

The layer region specifying unit 232 specifies the predetermined layer region in the tomographic image by analyzing the tomographic image acquired in step S2.

In some embodiments, without specifying the layer region in the tomographic image, the position to which the grayscale representation of the fundus image is to be applied is specified in the tomographic image by an operation using the operation unit 240B.

S32: Specify Pixel Position

Next, the main controller 211 controls the pixel position specifying unit 233 to specify the second position in the fundus image acquired in step S1. Here, the second position corresponds to the first position in the layer region (predetermined site) specified in step S31.

The pixel position specifying unit 233 specifies the second position in the fundus image corresponding to the first position in the tomographic image, as described above. The pixel position specifying unit 233 can specify the corresponding position in the fundus image for each pixel in the tomographic image.

S33: Correct Pixel Value

Subsequently, the main controller 211 controls the image correcting unit 234 to correct the pixel value(s) in the region including the first position in the tomographic image, based on the pixel value at the second position in the fundus image specified in step S32.

The image correcting unit 234 corrects the pixel value(s) in the image including the first position in the tomographic image, based on the pixel value at the second position in the fundus image specified in step S32, as described above. The image correcting unit 234 can correct the pixel value in the tomographic image, based on the pixel value at the corresponding position in the fundus image, for each pixel in the tomographic image.

This terminates the processing of step S3 in FIG. 11 (END).

In the embodiments described above, the case where the tomographic image is corrected in the ophthalmological apparatus including the OCT unit 100, and the like has been described. However, the configuration according to the embodiments is not limited thereto. For example, the ophthalmological information processing apparatus, which realizes the function of the data processor 230 shown in FIG. 4, may correct the tomographic image for the acquired OCT image (or the scan data), as described above. In this case, the OCT image (or the scan data) is acquired by an external OCT apparatus (ophthalmological apparatus).

Second Embodiment

In the first embodiment, the pixel value in the region including the predetermined position in the tomographic image is corrected based on the pixel value at the corresponding position in the fundus image, and the tomographic image in which the pixel value is corrected is displayed on the display unit 240A. However, the configuration of the ophthalmological apparatus (ophthalmological information processing apparatus) according to the embodiments is not limited to this. In a second embodiment, a second region corresponding to a first region in the fundus image is mapped to the first region, the first region including a predetermined position in the tomographic image.

In the following, the second embodiment will be described with a focus on differences from the first embodiment.

The configuration of the ophthalmological apparatus according to the second embodiment differs from that of the ophthalmological apparatus 1 according to the first embodiment in that a data processor 230a is provided in place of the data processor 230.

Figure 15:
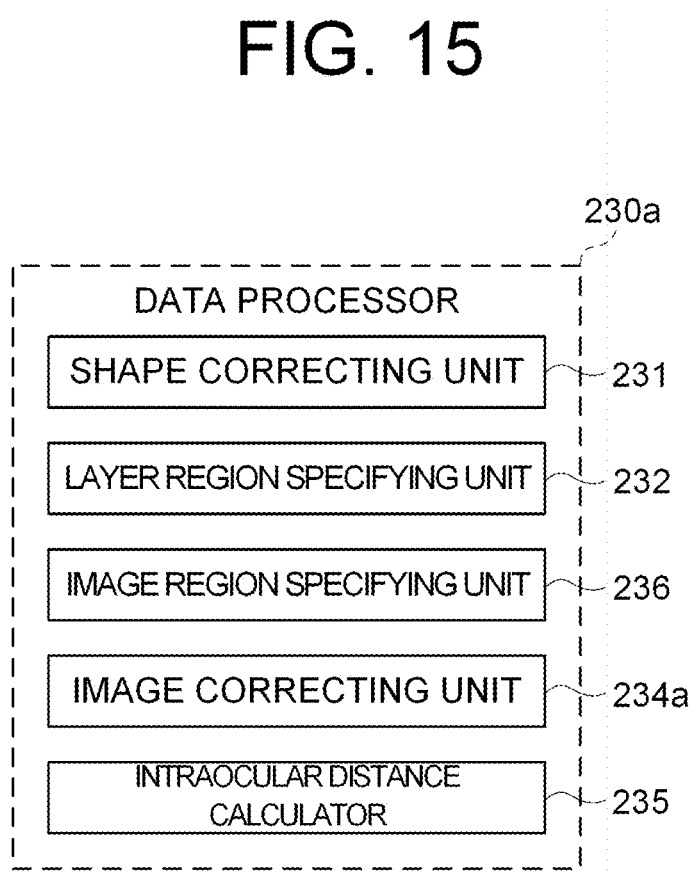
FIG. 15 is a schematic block diagram illustrating an example of the configuration of the ophthalmological apparatus according to the embodiments.

FIG. 15 shows a block diagram of an example of the configuration of the data processor 230a according to the present embodiment. In FIG. 15, parts similar to those in FIG. 4 are denoted by the same reference symbols, and description thereof is omitted as appropriate.

Such the data processor 230a includes the shape correcting unit 231, the layer region specifying unit 232, an image region specifying unit 236, an image correcting unit 234a, and the intraocular distance calculator 235.

The image region specifying unit 236 specifies a region in the color front image (fundus image) of the subject's eye E corresponding to at least a part of region in the layer region (predetermined site) specified by the layer region specifying unit 232. In some embodiments, the image region specifying unit 236 specifies a region in the front image corresponding to a region designated using the operation unit 240B for the image region corresponding to the layer region specified by the layer region specifying unit 232.

In some embodiments, the image region specifying unit 236 specifies the image region in the front image corresponding to an image region in the OCT image, using a reference position in the front image, a reference position in the OCT image, a position of a characteristic site of the subject's eye E depicted in the front image, and a position of the characteristic site depicted in the OCT image. Examples of the reference position in the front image include a position of the optical axis of the imaging optical system 30 in the front image. Examples of the reference position in the OCT image include a position of the optical axis of the interference optical system (optical system included in the OCT unit 100) in the OCT image. Examples of the characteristic site include an optic disc, a fovea, a blood vessel, a lesion, and a scar after treatment. In some embodiments, considering the magnification of the optical system, the image region in the front image corresponding to the image region in the OCT image is specified.

In some embodiments, the front image is acquired using the imaging optical system 30 under predetermined imaging conditions, and the OCT image is acquired using the OCT unit 100 under predetermined measurement conditions. In this case, by transforming the image region in the OCT image (or OCT image before correcting) according to the transformation equation corresponding to the imaging conditions and the measurement conditions (for example, a predetermined transformation equation), the image region specifying unit 236 specifies the image region in the front image of the subject's eye E corresponding to the image region in the OCT image.

Image Correction Unit

The image correcting unit 234a corrects the tomographic image by mapping a second region (image region) corresponding in the front image, the second region being specified by the image region specifying unit 236, to a first region of at least a part of the predetermined layer region (image region) in the tomographic image specified by the layer region specifying unit 232.

Figure 16:
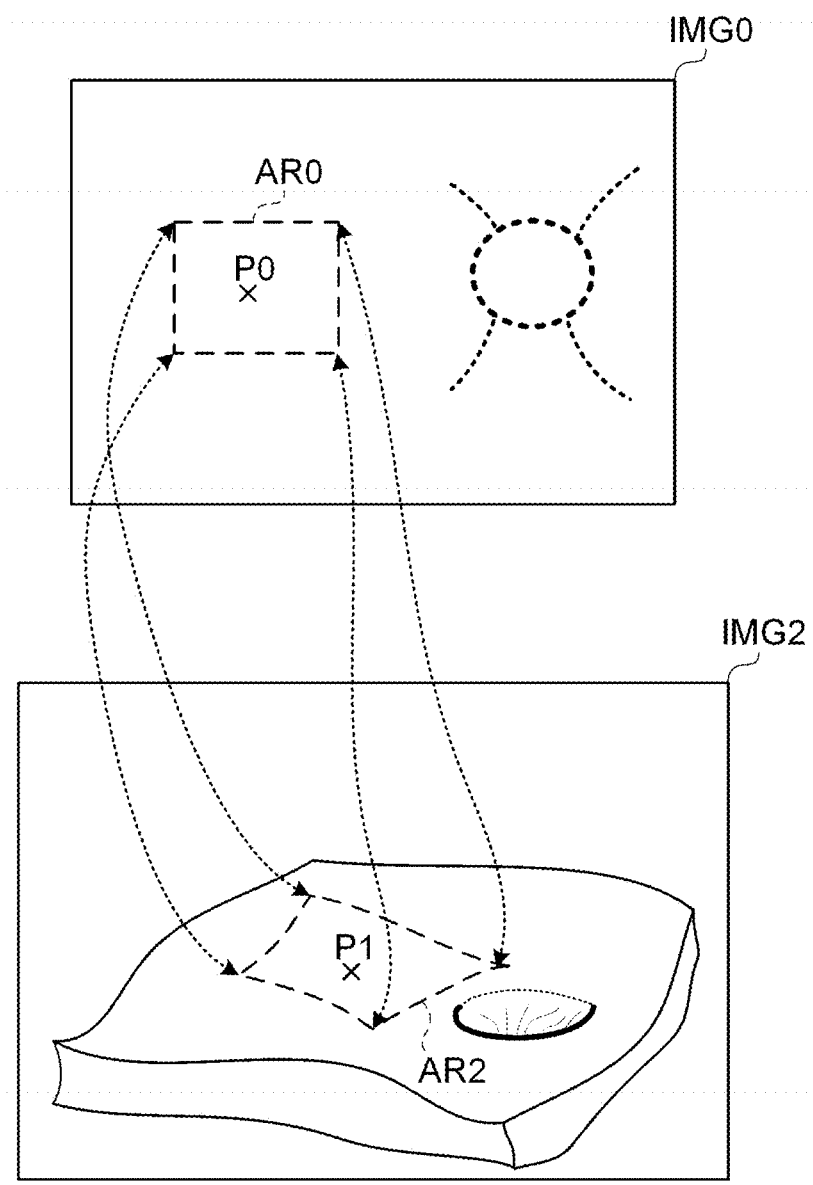
FIG. 16 is a schematic diagram for explaining processing performed by the ophthalmological apparatus according to the embodiments.

FIG. 16 shows a diagram describing the operation of the image region specifying unit 236 and the image correcting unit 234a according to the embodiments. FIG. 16 schematically represents the color front image IMG0 of the fundus Ef of the subject's eye E and the tomographic image IMG2 (three-dimensional OCT image) of the fundus Ef of the subject's eye E. In FIG. 16, the tomographic image IMG2 is the OCT image corrected by the shape correcting unit 231 or the OCT image before correcting.

As shown in FIG. 16, the image region specifying unit 236 specifies an image region AR0 (region including the second position P0) in the front image IMG0 of the subject's eye E corresponding to an image region AR2 (region including the first position P1) of at least a part of the predetermined layer region of the fundus in the tomographic image IMG2. The image correcting unit 234a corrects the tomographic image IMG2 by mapping the image region AR0 in the front image IMG0 to the image region AR2 in the tomographic image IMG1.

A known texture mapping process is used for the mapping processing executed by the image correcting unit 234a. For example, the image region AR2 is defined by three or more vertex positions (for example, four or more vertex positions in FIG. 16). The image region specifying unit 236 specifies the vertex position corresponding in the front image IMG0 for each of the three or more vertex positions in the tomographic image IMG2, and specifies the image region AR0 defined by the specified vertex positions. The pixel value of each pixel in the image region AR0 is obtained by interpolating the pixel values at the multiple vertex positions near the pixel.

This allows the image correcting unit 234a to acquire the tomographic image IMG2 in which the corresponding image region (image region AR0) in the front image is mapped to an arbitrarily shaped region (image region AR2) in the OCT image.

The controller 210 (main controller 211), as the display controller, can display the OCT image corrected by the image correcting unit 234a on the display unit 240A, in the same manner as in the first embodiment. Thereby, the grayscale representation in the fundus image is applied to a desired site in the tomographic image.

In FIG. 16, the case where the OCT image is a three-dimensional image has been described. However, the same applies to the case where the OCT image is a two-dimensional image.

The operation of the ophthalmological apparatus according to the present embodiment is almost the same as the first embodiment. However, in step S3 in FIG. 3, the processing is performed according to the following flow.

Figure 17:
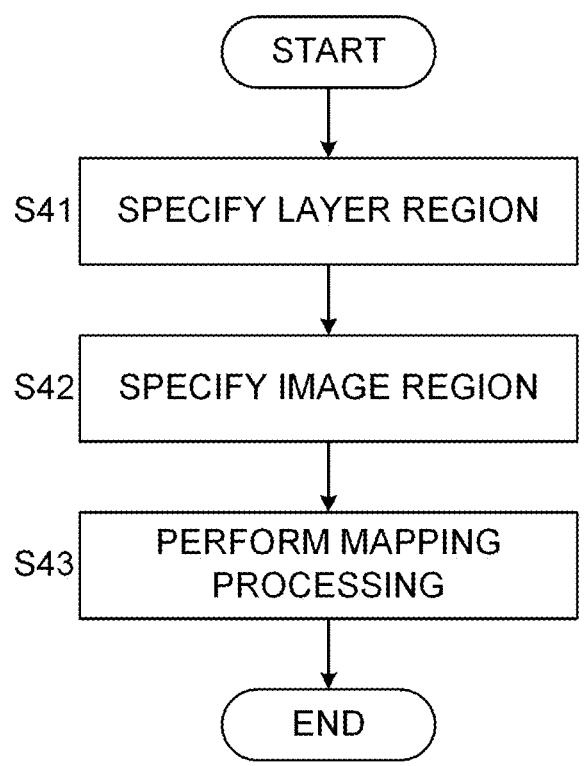
FIG. 17 is a schematic diagram illustrating an example of an operation of the ophthalmological apparatus according to the embodiments.

FIG. 17 shows an example of the operation of the ophthalmological apparatus according to the present embodiment. FIG. 17 shows a flowchart of an example of the operation of step S3 in FIG. 11. The storage unit 212 stores computer programs for realizing the processing shown in FIGS. 11 to 13 and 17. The main controller 211 operates according to the computer programs, and thereby the main controller 211 performs the processing shown in FIGS. 11 to 13, and 17.

41: Specify Layer Region

In step S3, the main controller 211 controls the layer region specifying unit 232 to specify the predetermined layer region in the tomographic image acquire in step S2, in the same manner as in step S31. In the present embodiment, the layer region to which the grayscale representation of the fundus image is applied is specified.

S42: Specify Image Region

Next, the main controller 211 controls the image region specifying unit 236 to specify the image region in the fundus image acquired in step S1. Here, the image region corresponds to the image region in the layer region specified in step S41.

The image region specifying unit 236 specifies the image region in the fundus image corresponding to the predetermined image region in the tomographic image, as described above. The image region specifying unit 236 can specify the corresponding image region in the fundus image for each of a plurality of image regions in the tomographic image.

S43: Perform Mapping Processing

Subsequently, the main controller 211 controls the image correcting unit 234a to correct the tomographic image by mapping the image region in the fundus image specified in step S42 to the image region in the tomographic image specified in step S41.

The image correcting unit 234a corrects the tomographic image by mapping the image region corresponding in the fundus image to the image region in the tomographic image, as described above. The image correcting unit 234a can map the image region corresponding in the fundus image for each of the image regions in the tomographic image.

This terminates the processing of step S3 in FIG. 11 (END).

Third Embodiment

In the embodiments described above, the tomographic image is corrected to apply the grayscale representation of the fundus image, and the corrected tomographic image is displayed. However, the configuration of the ophthalmological apparatus (ophthalmological information processing apparatus) according to the embodiments is not limited to this. In a third embodiment, on a region including a predetermined site in the tomographic image, a region corresponding in the fundus is overlaid, and is displayed.

In the following, the third embodiment will be described with a focus on differences from the first embodiment or the second embodiment.

The ophthalmological apparatus according to the third embodiment is almost the same configuration as that of the first embodiment or the second embodiment.

In the operation of the ophthalmological apparatus according to the present embodiment. the processing is performed according to the flow shown in FIG. 18, instead of the flow shown in FIG. 11.

FIG. 18 shows an example of the operation of the ophthalmological apparatus according to the present embodiment. FIG. 18 shows a flowchart of the operation example of the ophthalmological apparatus according to the present embodiment. Step S52 in FIG. 18 is the same as Step S2 in FIG. 12 (processing flow shown in FIG. 12 for details) is performed in the same way. The storage unit 212 stores computer programs for realizing the processing shown in FIG. 18 and FIG. 12. The main controller 211 operates according to the computer programs, and thereby the main controller 211 performs the processing shown in FIG. 18 and FIG. 12.

S51: Acquire Fundus Image

First, the main controller 211 perform alignment, in the same manner as in step S1.

S52: Acquire Tomographic Image

Subsequently, the main controller 211 controls the OCT unit 100 and the like to acquire tomographic image of the fundus Ef of the subject's eye E, in the same manner as in step S2. The details of step S52 are the same as in the processing flow shown in FIG. 2.

S53: Specify Layer Region

Next, the main controller 211 controls the layer region specifying unit 232 to specify the predetermined laver region in the tomographic image acquire in step S52, in the same manner as in step S31.

S54: Specify Image Region

Next, the main controller 211 controls the image region specifying unit 236 to specify the image region in the fundus image acquired in step S51. Here, the image region corresponds to the image region in the layer region specified in step S53.

The image region specifying unit 236 specifies the image region in the fundus image corresponding to the predetermined image region in the tomographic image, as described above. The image region specifying unit 236 can specify the corresponding image region in the fundus image for each of a plurality of image regions in the tomographic image.

S55: Overlay Display

The controller 210 (main controller 211) overlays the image region in the fundus image specified in step S54 on the predetermined image region in the tomographic image acquired in step S52, and displays them on the display unit 240A. In some embodiments, the controller 210 displays the fundus image acquired in step S51 and the tomographic image in which the corresponding image region in the fundus image is overlaid on the predetermined image region in the tomographic image on the display unit 240A.

This terminates the operation of the ophthalmological apparatus according to the present embodiment (END).

MODIFICATION EXAMPLES

In the above embodiments, the image correcting unit 234 or the image correcting unit 234a may correct the tomographic image by setting a predetermined pixel value to a predetermined layer region in a predetermined site in the tomographic image. For example, in the tomographic image, the pixel value in a first layer region in the predetermined site is corrected based on the fundus image, and the pixel value in a second layer region (layer region deeper or shallower than the first layer region) in the predetermined site is set to a pixel value determined in advance. This allows to identifiably display the layer region depicted in the tomographic image while the grayscale representation of the fundus image is applied.

In some embodiments, a program for causing a computer to execute the method of controlling the ophthalmological apparatus described above is provided. Such a program can be stored in any computer-readable recording medium (for example, a non-transitory computer readable medium). Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

Effects

Hereinafter, the ophthalmological information processing apparatus, the ophthalmological apparatus, the ophthalmological information processing method, and the program according to the embodiments will be described.

An ophthalmological information processing apparatus (for example, an apparatus including the data processor 230) according to some embodiments includes an acquisition unit (the imaging optical system 30, the optical system in the path from the interference optical system included in the OCT unit 100 to the objective lens 22, and the image forming unit 220, or the optical system in the path from the interference optical system included in the OCT unit 100 to the objective lens 22, the image forming unit 220, and the data processor 230), and an image correcting unit (234, 234a). The acquisition unit is configured to acquire a front image (fundus image) depicting a predetermined site of a subject's eye (E) in multiple gradations and an OCT image (tomographic image) of the subject's eye. The image correcting unit is configured to correct a pixel value in a region including a first position (P1) of the predetermined site in the OCT image based on a pixel value at a second position (P0) corresponding to the first position in the front image.

According to such a configuration, the grayscale representation of the predetermined site in the front image of the subject's eye can be applied to the OCT image depicting the site. In general, the front image of the subject's eye has a higher image quality than the OCT image. This allows to easily grasp the morphology of the predetermined site in the subject's eye from the OCT image.

The ophthalmological information processing apparatus according to some embodiments further includes a shape correcting unit (231) configured to correct a shape of the predetermined site so as to follow a traveling direction of measurement light (LS) for acquiring the OCT image to generate a correction OCT image. The image correcting unit is configured to correct the pixel value in the region in the correction OCT image.

According to such a configuration, with the shape of the predetermined region of the subject's eye corrected to the actual shape, the grayscale representation of the predetermined site in the front image of the subject's eye can be applied to the OCT image depicting the site. This allows to grasp the morphology of the predetermined site in the subject's eye from the OCT image in more detail.

The ophthalmological information processing apparatus according to some embodiments further includes a position specifying unit (pixel position specifying unit 233) configured to specify the second position corresponding to the first position. The image correcting unit is configured to correct the pixel value at the specified second position based on the pixel value at the first position.

According to such a configuration, the OCT image is corrected using the pixel value at the position corresponding to the OCT image in the front image. Thereby, the grayscale representation of the predetermined site in the front image of the subject's eye can be easily applied to the OCT image.

The ophthalmological information processing apparatus according to some embodiments further includes a layer region specifying unit (232) configured to specify a predetermined layer region in the OCT image. The image correcting unit is configured to correct the OCT image by mapping an image region in the front image to at least a part of the predetermined layer region in the OCT image.

According to such a configuration, the OCT image is corrected by mapping the image region in the front image. Here, the image region corresponds to the layer region in the OCT image. Thereby, the grayscale representation of the predetermined site in the front image of the subject's eye can be easily applied to the OCT image.

In the ophthalmological information processing apparatus according to some embodiments, the image correcting unit is configured to correct the OCT image by setting a predetermined layer region of the predetermined site in the OCT image to a predetermined pixel value.

According to such a configuration, the OCT image capable of identifying a desired layer region depicted in the OCT image can be acquired.

The ophthalmological information processing apparatus according to some embodiments further includes a display controller (controller 210, main controller 211) configured to display the OCT image corrected by the image correcting unit on a display means (display apparatus 3, display unit 240A).

According such a configuration, the OCT image capable of grasping the morphology of the predetermined site of the subject's eye can be displayed.

An ophthalmological information processing apparatus according to some embodiments includes an acquisition unit (the imaging optical system 30, the optical system in the path from the interference optical system included in the OCT unit 100 to the objective lens 22, and the image forming unit 220, or the optical system in the path from the interference optical system included in the OCT unit 100 to the objective lens 22, the image forming unit 220, and the data processor 230), and a display controller (controller 210, main controller 211). The acquisition unit is configured to acquire a front image (fundus image) depicting a predetermined site of a subject's eye (E) in multiple gradations and an OCT image (tomographic image) of the subject's eye. The display controller is configured to display a region including a first position in the predetermined site in the OCT image on a display means (display apparatus 3, display unit 240A), based on a pixel value at a second position corresponding to the first position in the front image.

According to such a configuration, the grayscale representation of the predetermined site in the front image of the subject's eye can be applied to the OCT image depicting the site. This allows to easily grasp the morphology of the predetermined site in the subject's eye from the OCT image.

The ophthalmological information processing apparatus according to some embodiments further includes a shape correcting unit (231) configured to correct a shape of the predetermined site so as to follow a traveling direction of measurement light (LS) for acquiring the OCT image to generate a correction OCT image. The display controller is configured to display a region including a first position in the predetermined site in the correction OCT image on the display means, based on a pixel value at the second position in the front image.

According to such a configuration, with the shape of the predetermined region of the subject's eye corrected to the actual shape, the grayscale representation of the predetermined site in the front image of the subject's eye can be applied to the OCT image depicting the site. This allows to grasp the morphology of the predetermined site in the subject's eye from the OCT image in more detail.

In the ophthalmological information processing apparatus according to some embodiments, the predetermined site is a fundus or vicinity of the fundus.

According such a configuration, the morphology of the fundus of the subject's eye or the vicinity thereof can be easily grasped from the OCT image.

In the ophthalmological information processing apparatus according to some embodiments, the front image is a color image depicting the predetermined site using two or more color components.

According to such a configuration, the morphology of the predetermined site in the subject's eye can be easily grasped from the OCT image in which the predetermined region id depicted using two or more color components.

An ophthalmological apparatus (1) according to some embodiments includes an imaging unit (imaging optical system 30) configured to image the predetermined site; an OCT unit (the imaging optical system 30, the optical system in the path from the interference optical system included in the OCT unit 100 to the objective lens 22, and the image forming unit 220, or the optical system in the path from the interference optical system included in the OCT unit 100 to the objective lens 22, the image forming unit 220, and the data processor 230) configured to acquire the OCT image; and the ophthalmological information processing apparatus described in any of the above.

According to such a configuration, the ophthalmological apparatus capable of applying the grayscale representation of the predetermined site in the front image of the subject's eye to the OCT image depicting the site can be provided.

An ophthalmological information processing method according to some embodiments includes an acquisition step and an image correcting step. The acquisition step is performed to acquire a front image (fundus image) depicting a predetermined site of a subject's eye (E) in multiple gradations and an OCT image (tomographic image) of the subject's eye. The image correcting step is performed to correct a pixel value in a region including a first position of the predetermined site in the OCT image based on a pixel value at a second position corresponding to the first position in the front image.

According to such a method, the grayscale representation of the predetermined site in the front image of the subject's eye can be applied to the OCT image depicting the site. In general, the front image of the subject's eye has a higher image quality than the OCT image. This allows to easily grasp the morphology of the predetermined site in the subject's eye from the OCT image.

The ophthalmological information processing method according to some embodiments further includes a shape correcting step of correcting a shape of the predetermined site so as to follow a traveling direction of measurement light (LS) for acquiring the OCT image to generate a correction OCT image. The image correcting step is performed to correct the pixel value in the region in the correction OCT image.

According to such a method, with the shape of the predetermined region of the subject's eye corrected to the actual shape, the grayscale representation of the predetermined site in the front image of the subject's eye can be applied to the OCT image depicting the site. This allows to grasp the morphology of the predetermined site in the subject's eye from the OCT image in more detail.

The ophthalmological information processing method according to some embodiments further includes a layer region specifying step of specifying a predetermined layer region in the OCT image. The image correcting step is performed to correct the OCT image by mapping an image region in the front image to at least a part of the predetermined layer region in the OCT image.

According to such a method, the OCT image is corrected by mapping the image region in the front image. Here, the image region corresponds to the layer region in the OCT image. Thereby, the grayscale representation of the predetermined site in the front image of the subject's eye can be easily applied to the OCT image.

In the ophthalmological information processing method according to some embodiments, the image correcting step is performed to correct the OCT image by setting a predetermined layer region of the predetermined site in the OCT image to a predetermined pixel value.

According to such a method, the OCT image capable of identifying a desired layer region depicted in the OCT image can be acquired.

The ophthalmological information processing method according to some embodiments further includes a display control step of displaying the OCT image corrected in the image correcting step on a display means (display apparatus 3, display unit 240A).

According such a method, the OCT image capable of grasping the morphology of the predetermined site of the subject's eye can be displayed.

An ophthalmological information processing method according to the embodiments includes an acquisition step and a display control step. The acquisition step is performed to acquire a front image (fundus image) depicting a predetermined site of a subject's eye (E) in multiple gradations and an OCT image (tomographic image) of the subject's eye. The display control step is performed to display a region including a first position in the predetermined site in the OCT image on a display means, based on a pixel value at a second position corresponding to the first position in the front image.

According to such a method, the grayscale representation of the predetermined site in the front image of the subject's eye can be applied to the OCT image depicting the site. This allows to easily grasp the morphology of the predetermined site in the subject's eye from the OCT image.

The ophthalmological information processing method according to some embodiments further includes a shape correcting step of correcting a shape of the predetermined site so as to follow a traveling direction of measurement light (LS) for acquiring the OCT image to generate a correction OCT image. The display control step is performed to display a region including a first position in the predetermined site in the correction OCT image on the display means, based on a pixel value at the second position in the front image.

According to such a method, with the shape of the predetermined region of the subject's eye corrected to the actual shape, the grayscale representation of the predetermined site in the front image of the subject's eye can be applied to the OCT image depicting the site. This allows to grasp the morphology of the predetermined site in the subject's eye from the OCT image in more detail.

In the ophthalmological information processing method according to some embodiments, the predetermined site is a fundus or vicinity of the fundus.

According such a method, the morphology of the fundus of the subject's eye or the vicinity thereof can be easily grasped from the OCT image.

A program according to some embodiments causes a computer to execute each step of the ophthalmological information processing method described in any of the above.

According to such a program, the program capable of applying the grayscale representation of the predetermined site in the front image of the subject's eye to the OCT image depicting the site can be provided. Thereby, the program capable of easily grasping the morphology of the predetermined site in the subject's eye from the OCT image can be provided.

Others

The above-described some embodiments or the modification examples thereof are merely examples for carrying out the present invention. Those who intend to implement the present invention can apply any modification, omission, addition, or the like within the scope of the gist of the present invention.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV,* 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms: furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmological information processing apparatus, comprising:
    an acquisition unit including at least one lens and configured to acquire a front image depicting a predetermined site of a subject's eye in multiple gradations and an optical coherence tomography (OCT) image of the subject's eye; and
    processing circuitry configured as an image correcting unit configured to correct a pixel value in a region including a first position of the predetermined site in the OCT image based on a pixel value at a second position corresponding to the first position in the front image, wherein
    the processing circuitry is further configured as a shape correcting unit configured to correct a shape of the predetermined site so as to follow a traveling direction of measurement light for acquiring the OCT image to generate a correction OCT image,
    the image correcting unit is configured to correct the pixel value in the region in the correction OCT image,
    the acquisition unit is further configured to acquire the OCT image using the measurement light deflected around a scan center position on the subject's eye, and
    the shape correcting unit is further configured to interpolate pixels between A-scan images adjacent to each other according to a depth position in the A-scan image to generate the correction OCT image.

2. The ophthalmological information processing apparatus of claim 1, wherein
    the processing circuitry is further configured as a position specifying unit configured to specify the second position corresponding to the first position, and
    the image correcting unit is configured to correct the pixel value at the specified second position based on the pixel value at the first position.

3. The ophthalmological information processing apparatus of claim 1, wherein
    the processing circuitry is further configured as a layer region specifying unit configured to specify a predetermined layer region in the OCT image, and
    the image correcting unit is configured to correct the OCT image by mapping an image region in the front image to at least a part of the predetermined layer region in the OCT image.

4. The ophthalmological information processing apparatus of claim 1, wherein the image correcting unit is configured to correct the OCT image by setting a predetermined layer region of the predetermined site in the OCT image to a predetermined pixel value.

5. The ophthalmological information processing apparatus of claim 1, wherein
the processing circuitry is further configured as a display controller configured to display the OCT image corrected by the image correcting unit on a display.

6. The ophthalmological information processing apparatus of claim 1, wherein
the predetermined site is a fundus or vicinity of the fundus.

7. The ophthalmological information processing apparatus of claim 1, wherein
the front image is a color image depicting the predetermined site using two or more color components.

8. An ophthalmological information processing apparatus, comprising:
an acquisition unit including at least one lens and configured to acquire a front image depicting a predetermined site of a subject's eye in multiple gradations and an optical coherence tomography (OCT) image of the subject's eye; and
processing circuitry configured as a display controller configured to display a region including a first position in the predetermined site in the OCT image on a display, based on a pixel value at a second position corresponding to the first position in the front image, wherein
the processing circuitry is further configured as a shape correcting unit configured to correct a shape of the predetermined site so as to follow a traveling direction of measurement light for acquiring the OCT image to generate a correction OCT image,
the display controller is configured to display a region including a first position in the predetermined site in the correction OCT image on the display, based on a pixel value at the second position in the front image,
the acquisition unit is further configured to acquire the OCT image using the measurement light deflected around a scan center position on the subject's eye, and
the shape correcting unit is further configured to interpolate pixels between A-scan images adjacent to each other according to a depth position in the A-scan image to generate the correction OCT image.

9. The ophthalmological information processing apparatus of claim 8, wherein
the predetermined site is a fundus or vicinity of the fundus.

10. The ophthalmological information processing apparatus of claim 8, wherein
the front image is a color image depicting the predetermined site using two or more color components.

11. An ophthalmological apparatus, comprising:
an imaging unit including at least one lens and configured to image a predetermined site to acquire a front image depicting the predetermined site of the subject's eye in multiple gradations;
an optical coherence tomography (OCT) unit including an OCT scanner and configured to generate an OCT image; and
an ophthalmological information processing apparatus including processing circuitry configured as an image correcting unit configured to correct a pixel value in a region including a first position of the predetermined site in the OCT image based on a pixel value at a second position corresponding to the first position in the front image, wherein
the processing circuitry is further configured as a shape correcting unit configured to correct a shape of the predetermined site so as to follow a traveling direction of measurement light for acquiring the OCT image to generate a correction OCT image,
the image correcting unit is configured to correct the pixel value in the region in the correction OCT image,
the OCT unit is further configured to acquire the OCT image using the measurement light deflected around a scan center position on the subject's eye, and
the shape correcting unit is further configured to interpolate pixels between A-scan images adjacent to each other according to a depth position in the A-scan image to generate the correction OCT image.

12. An ophthalmological apparatus, comprising:
an imaging unit including at least one lens and configured to image a front image depicting a predetermined site of a subject's eye in multiple gradations;
an optical coherence tomography (OCT) unit including an OCT scanner and configured to acquire an OCT image of the subject's eye; and
an ophthalmological information processing apparatus that includes processing circuitry configured as a display controller configured to display a region including a first position in the predetermined site in the OCT image on a display, based on a pixel value at a second position corresponding to the first position in the front image, wherein
the processing circuitry is further configured as a shape correcting unit configured to correct a shape of the predetermined site so as to follow a traveling direction of measurement light for acquiring the OCT image to generate a correction OCT image,
the display controller is configured to display a region including a first position in the predetermined site in the correction OCT image on the display, based on a pixel value at the second position in the front image,
the OCT unit is further configured to acquire the OCT image using the measurement light deflected around a scan center position on the subject's eye, and
the shape correcting unit is further configured to interpolate pixels between A-scan images adjacent to each other according to a depth position in the A-scan image to generate the correction OCT image.

13. An ophthalmological information processing method, comprising:
acquiring a front image depicting a predetermined site of a subject's eye in multiple gradations and an optical coherence tomography (OCT) image of the subject's eye;
image correcting a pixel value in a region including a first position of the predetermined site in the OCT image based on a pixel value at a second position corresponding to the first position in the front image; and
shape correcting a shape of the predetermined site so as to follow a traveling direction of measurement light for acquiring the OCT image to generate a correction OCT image, wherein
the image correcting is performed to correct the pixel value in the region in the correction OCT image,
the acquiring acquires the OCT image using the measurement light deflected around a scan center position on the subject's eye, and the shape correcting includes interpolating pixels between A-scan images adjacent to each other according to a depth position in the A-scan image to generate the correction OCT image.

14. The ophthalmological information processing method of claim 13, further comprising
specifying a predetermined layer region in the OCT image, wherein
the image correcting performed to correct the OCT image by mapping an image region in the front image to at least a part of the predetermined layer region in the OCT image.

15. The ophthalmological information processing method of claim 13, wherein
the image correcting performed to correct the OCT image by setting a predetermined layer region of the predetermined site in the OCT image to a predetermined pixel value.

16. The ophthalmological information processing method of claim 13, further comprising
displaying the OCT image corrected in the image correcting on a display.

17. The ophthalmological information processing method of claim 13, wherein
the predetermined site is a fundus or vicinity of the fundus.

18. A non-transitory computer readable recording medium storing a program of causing a computer to execute each step of the ophthalmological information processing method of claim 13.

19. An ophthalmological information processing method, comprising:
acquiring a front image depicting a predetermined site of a subject's eye in multiple gradations and an optical coherence tomography (OCT) image of the subject's eye; and
displaying a region including a first position in the predetermined site in the OCT image on a display, based on a pixel value at a second position corresponding to the first position in the front image; and
correcting a shape of the predetermined site so as to follow a traveling direction of measurement light for acquiring the OCT image to generate a correction OCT image, wherein
the displaying the region is performed to display a region including a first position in the predetermined site in the correction OCT image on the display, based on a pixel value at the second position in the front image,
the acquiring acquires the OCT image using the measurement light deflected around a scan center position on the subject's eye,
the shape correcting includes interpolating pixels between A-scan images adjacent to each other according to a depth position in the A-scan image to generate the correction OCT image.

20. The ophthalmological information processing method of claim 19, wherein
the predetermined site is a fundus or vicinity of the fundus.

21. A non-transitory computer readable recording medium storing a program of causing a computer to execute each step of the ophthalmological information processing method of claim 19.

* * * * *